(12) United States Patent
Bushnell et al.

(10) Patent No.: US 6,849,233 B2
(45) Date of Patent: Feb. 1, 2005

(54) VACUUM STERILIZED SEALING OF PASSTHROUGH LIGHT TREATMENT DEVICES

(75) Inventors: Andrew H. Bushnell, San Diego, CA (US); William M. Fries, San Diego, CA (US)

(73) Assignee: PurePulse Technologies, Inc., CA (US)

(*) Notice: Subject to any disclaimer, the term of this patent is extended or adjusted under 35 U.S.C. 154(b) by 698 days.

(21) Appl. No.: 09/794,594

(22) Filed: Feb. 26, 2001

(65) Prior Publication Data

US 2002/0119072 A1 Aug. 29, 2002

(51) Int. Cl.⁷ ................................................. A61L 2/10
(52) U.S. Cl. .......................... 422/24; 277/642; 312/1; 250/453.11
(58) Field of Search .................... 422/24; 277/634, 277/641, 642, 650; 49/477.1; 220/239, 378; 141/98, 346; 312/1; 250/453.11, 455.11

(56) References Cited

U.S. PATENT DOCUMENTS

| | | |
|---|---|---|
| 3,117,832 A | 1/1964 | Thomas |
| 3,414,120 A | 12/1968 | Sellers |
| 4,366,125 A | 12/1982 | Kodera et al. |
| 4,469,335 A | 9/1984 | Moore |
| 4,512,498 A | 4/1985 | Leibinger |
| 5,114,670 A | 5/1992 | Duffey |
| 5,446,289 A | 8/1995 | Shodeen et al. |
| 5,732,843 A * | 3/1998 | Glachet et al. ............ 220/315 |
| 6,030,578 A | 2/2000 | McDonald |
| 6,048,493 A | 4/2000 | Melgaard et al. |
| 6,307,206 B1 * | 10/2001 | Riviere et al. ......... 250/453.11 |

FOREIGN PATENT DOCUMENTS

| | | |
|---|---|---|
| CA | 1227012 | 9/1987 |
| DE | 1241561 | 6/1967 |
| EP | 0580176 A1 | 1/1994 |
| JP | 9010283 | 1/1997 |
| WO | WO 96/21615 A2 | 7/1996 |
| WO | WO 98/33719 A1 | 8/1998 |

* cited by examiner

Primary Examiner—E. Leigh McKane
(74) Attorney, Agent, or Firm—Thomas F. Lebens; Fitch, Even, Tabin & Flannery

(57) ABSTRACT

A vacuum-sealable hatch that is vacuum sealed to a surface of a passthrough light sterilization device, and related methods of use, consists of a hatch body having at least a portion adapted to fit within an opening of the treatment chamber and a flexible piece attached to the hatch body. The flexible piece extends peripherally from the hatch body and includes a seating portion which is adapted to be vacuum sealed to a seating region of an interior surface of the treatment chamber. The hatch body and the flexible piece seal the treatment chamber from the outside environment, thereby preventing the free flow of microorganisms to and from the treatment chamber and the outside environment. In some variations, at least the seating portion of the flexible piece is transmissive to the light treatment such that surfaces underneath the seating region are treated by the light treatment.

48 Claims, 16 Drawing Sheets

VACUUM STERILIZED SEALING OF PASSTHROUGH LIGHT TREATMENT DEVICES

This patent document relates to passthrough sterilization devices described in U.S. patent application Ser. No. 09/580,361, filed May 26, 2000, of Cooper et al., for BROAD-SPECTRUM PULSED LIGHT PASSTHROUGH STERILIZATION DEVICE, now abandoned which is incorporated herein by reference.

BACKGROUND OF THE INVENTION

1. Field of the Invention

The present invention relates to the light treatment chambers for treating objects placed therein, and more particularly to the sealing the light treatment chamber from the outside environment. Even more particularly, the present invention relates to a hatch for sealing an opening of the light treatment chamber from the outside environment.

2. Discussion of the Related Art

A light treatment chamber is a device in which objects are treated with light to deactivate microorganisms on the objects. A passthrough treatment device is generally known in the art as a treatment device including a treatment chamber into which non-sterile objects are placed into from a "contaminated" or non-sterile environment, treated within the treatment chamber, and then retrieved out of the treatment chamber into a "clean" or sterile environment, such as within an isolation barrier or chamber. Passthrough treatment devices are commonly used in medical and pharmaceutical applications where items, such as operating instruments or pharmaceutical devices, are placed within the treatment chamber, treated, and then retrieved into the sterile environment. Thus, contaminants from the non-sterile environment are deactivated prior to entry into the sterile environment. Typically only one side of the passthrough treatment chamber, or door to the passthrough treatment chamber, is open at a time, to prevent the free flow of air-borne contaminants into the sterile environment.

Many techniques are used to deactivate organisms on the surface of the objects prior to being inserted into a sterile environment. One example is through the use of continuous wave ultraviolet light (also referred to as UV light) directed at the object to be transferred into the sterile environment. The ultraviolet light is typically provided by low-pressure Mercury vapor lamps, which emit UV light at about 253 nm. An example of such an ultraviolet passthrough device is shown in U.S. Pat. No. 5,446,289, entitled ULTRAVIOLET PASSTHROUGH STERILIZATION DEVICE, issued to Shodeen et al. (hereinafter referred to as the '289 patent). The object is placed into the treatment chamber of the UV passthrough device from a non-sterile environment through a first door. The first door is closed; thus, sealing the treatment chamber from the non-sterile environment and then the treatment chamber is irradiated with the UV light, generated by Mercury lamps, for about 30 seconds to 3 minutes at about 2000–6000 micro watts per square centimeter. For most applications, this is sufficient to deactivate most organisms on the object. However, sterilization of the object and the treatment chamber is not achieved in such devices, with microbial deactivation being only on the order of 4 or 5 logs reduction (whereas 6 to 7 logs reduction is generally recognized as sufficient to constitute sterilization). The object is then removed from the treatment chamber by opening a second door that is exposed to the sterile environment and removing the item.

An important feature of the passthrough device, such as that shown in the '289 patent, is that the treatment chamber, also referred to as the "treatment cell" or the "treatment zone", must be sealed from both the non-sterile environment and the sterile environment when microorganisms are being treated with, e.g., the ultraviolet light. And, at least one end of the treatment chamber must always be sealed to prevent the flow of microorganisms between the sterile and non-sterile environments. There are many types of sealing devices available for use in such passthrough devices. The most common is a sealed door system, as shown in the '289 patent, having a first and second door. Thus, the first door has an open position such that an operator can access the treatment chamber (e.g. to place an object to be sterilized therein) through an opening and a closed position such that the first door engages the opening in the treatment chamber. Similarly, the second door also has an open position such that the operator can access the treatment chamber from the sterile environment via another opening (e.g. removing the object having been sterilized within the treatment chamber) and a closed position, such that the second door engages the other opening in the treatment chamber.

Both the first and second doors incorporate molded seals and gaskets to effectuate the seal between the openings of the treatment chamber and the respective doors; thus, sealing the sterile environment from the non-sterile environment. Mechanical pressure is typically applied to each door against the portion of the treatment chamber that contacts the door (i.e. the contact area between the door and the treatment chamber is typically at the opening). Typically, a seal or gasket is positioned at the opening of the treatment chamber and/or another seal or gasket is positioned around the edges of the door. This mechanical pressure is typically the force applied as the door is snugly closed against the opening, or within the opening.

Additionally, the door is designed with some type of locking device that maintains this mechanical pressure on the door against the contact area between the door and the treatment chamber. Examples of such locking devices include a latch system, such as found in common mechanical door designs, or a lever or arm that is rigidly moved in position over the door once closed to physically hold the door in position against the appropriate seals or gaskets with a desired amount of force to effectuate the seal.

One problem associated with sealed door systems and other mechanical sealing devices is that they may be structurally complicated requiring precisely cut or molded seals and/or gaskets that conform to the specific dimension of the door and/or the area that the seals are designed to contact, e.g. the seals must conform precisely to an opening of the treatment chamber. Thus, if one or more seals are imperfect in shape, the sealing of the treatment chamber may not be complete. Furthermore, over time, the seals or gaskets may physically degrade due to repeated exposure to the light source used in the treatment; thus, compromising the effective seal created between the door and opening to the treatment chamber.

Additionally, another problem is that the door itself or the structure holding the door, e.g. the hinge or arm handle, may become slightly deformed (e.g. warped due to the weight of the door or other pressure applied to the door), which may affect the evenness of the pressure applied to the contact area between the door and opening to the treatment chamber. For example, in the closed position, the door may not apply an even amount of pressure to all areas of the seals at different contact points. Furthermore, the locking device, e.g. a latch or lever, may not hold the door against or within the opening to the treatment chamber with an even amount of pressure or force, or even hold the door with the appropriate amount of force. For example, although the seals, the door, the hinges, the arms, etc., may be structurally perfect and be able to seal the door within the opening to the treatment chamber with the proper alignment and pressure, the locking device may not properly retain the door within the opening with the appropriate pressure due to physical deformities in the locking device. Thus, disadvantageously, the seals may not be held together effectively and the seal formed may be compromised.

What is needed is a structurally simple and easily replaceable sterilized seal for a light treatment chamber, such as a passthrough treatment device, as an alternative to the common sealed door system using molded seals or gaskets. The present invention advantageously addresses the above and other needs.

SUMMARY OF THE INVENTION

The present invention advantageously addresses the needs above as well as other needs by providing a vacuum sterilized seal for a passthrough device that passes items from a non-sterile environment into a sterile environment and that is both structurally simple and easily replaceable.

In one embodiment, the invention can be characterized as a vacuum-sealable hatch for sealing a treatment chamber from an outside environment including a hatch body having at least a portion adapted to fit within an opening of the treatment chamber and a flexible piece attached to the hatch body. The flexible piece extends peripherally from the hatch body and includes a seating portion which is adapted to be vacuum sealed to a seating region of an interior surface of the treatment chamber. The hatch body and the flexible piece seal the treatment chamber from the outside environment, thereby preventing the free flow of microorganisms to and from the treatment chamber and the outside environment.

In another embodiment, the invention can be characterized as a hatch for sealing a light treatment chamber from an outside environment including a hatch body having at least a portion adapted to fit within an opening of the light treatment chamber and a flexible piece attached to the hatch body. The flexible piece extends peripherally from the hatch body. A seating portion of the flexible piece is adapted to be sealed to a seating region of an interior surface of the light treatment chamber. The hatch body and the flexible piece seal the light treatment chamber from the outside environment and at least the seating portion of the flexible piece is light transmissive such that at least the seating region is treated by light from the light treatment chamber.

In yet another embodiment, the invention can be characterized as a light treatment device including a treatment chamber having an opening accessible from an outside environment and a seating region proximate to the opening. Also included are one or more lamps within the treatment chamber for producing light within the treatment chamber, wherein the light is used to deactivate microorganisms within the treatment chamber. Also included are one or more vacuum ports at the seating region, a hatch body having at least a portion adapted to fit within the opening and a flexible piece attached to the hatch body. The flexible piece has a periphery portion including a seating portion, wherein the periphery portion of the flexible piece overlaps the hatch body and the seating portion is adapted to be vacuum sealed to the seating region. The hatch body and flexible piece seal the treatment chamber from the outside environment.

In an additional embodiment, the invention can be characterized as a sterilizable vacuum sealing surface of a treatment chamber of a light treatment device including an inner wall of the treatment chamber. The treatment chamber defines a volume within which objects are treated with light for the reduction of microorganisms. Also included is an opening formed within the inner wall for providing access to the treatment chamber from an outside environment and a seating region in the inner wall proximate to a periphery of the opening. Also included are one or more vacuum ports at the seating region for forming a vacuum seal between the seating region and materials placed against the seating region.

In a further embodiment, the invention can be characterized as a method of sealing a treatment chamber of a light treatment device from an outside environment including the steps of: placing at least a portion of a hatch body within an opening of the treatment chamber, wherein the hatch body includes a flexible piece attached to the hatch body, wherein a periphery portion of the flexible piece overlaps the hatch body; positioning the at least the portion of the hatch body within the opening such that a seating portion of the periphery portion is within the treatment chamber and contacts an inner surface of the treatment chamber; and creating a vacuum seal between the inner surface of the treatment chamber and the seating portion of the flexible piece, wherein the flexible piece and the hatch body seal the treatment chamber from the outside environment.

In yet another embodiment, the invention can be characterized as a method of treating and passing an object from a non-sterile environment into a substantially sterile environment including the steps: pre-sterilizing a treatment chamber; vacuum sealing the treatment chamber from the substantially sterile environment; placing the object into the treatment chamber from the non-sterile environment; sealing the non-sterile environment from the treatment chamber; illuminating the object with light, wherein organisms present on the object are deactivated; unsealing the treatment chamber from the substantially sterile environment; and removing the object from the treatment chamber into the substantially sterile environment.

BRIEF DESCRIPTION OF THE DRAWINGS

The above and other aspects, features and advantages of the present invention will be more apparent from the following more particular description thereof, presented in conjunction with the following drawings wherein:

FIGS. 2A–2H are lengthwise cross sectional views of the sterilized vacuum seal formed with the vacuum-sealable hatch of FIG. 1 during operation at the various stages during use of the passthrough treatment device of FIG. 1;

Corresponding reference characters indicate corresponding components throughout the several views of the drawings.

DETAILED DESCRIPTION OF THE PREFERRED EMBODIMENTS

The following description of the presently contemplated best mode of practicing the invention is not to be taken in a limiting sense, but is made merely for the purpose of describing the general principles of the invention. The scope of the invention should be determined with reference to the claims.

Figure 1:
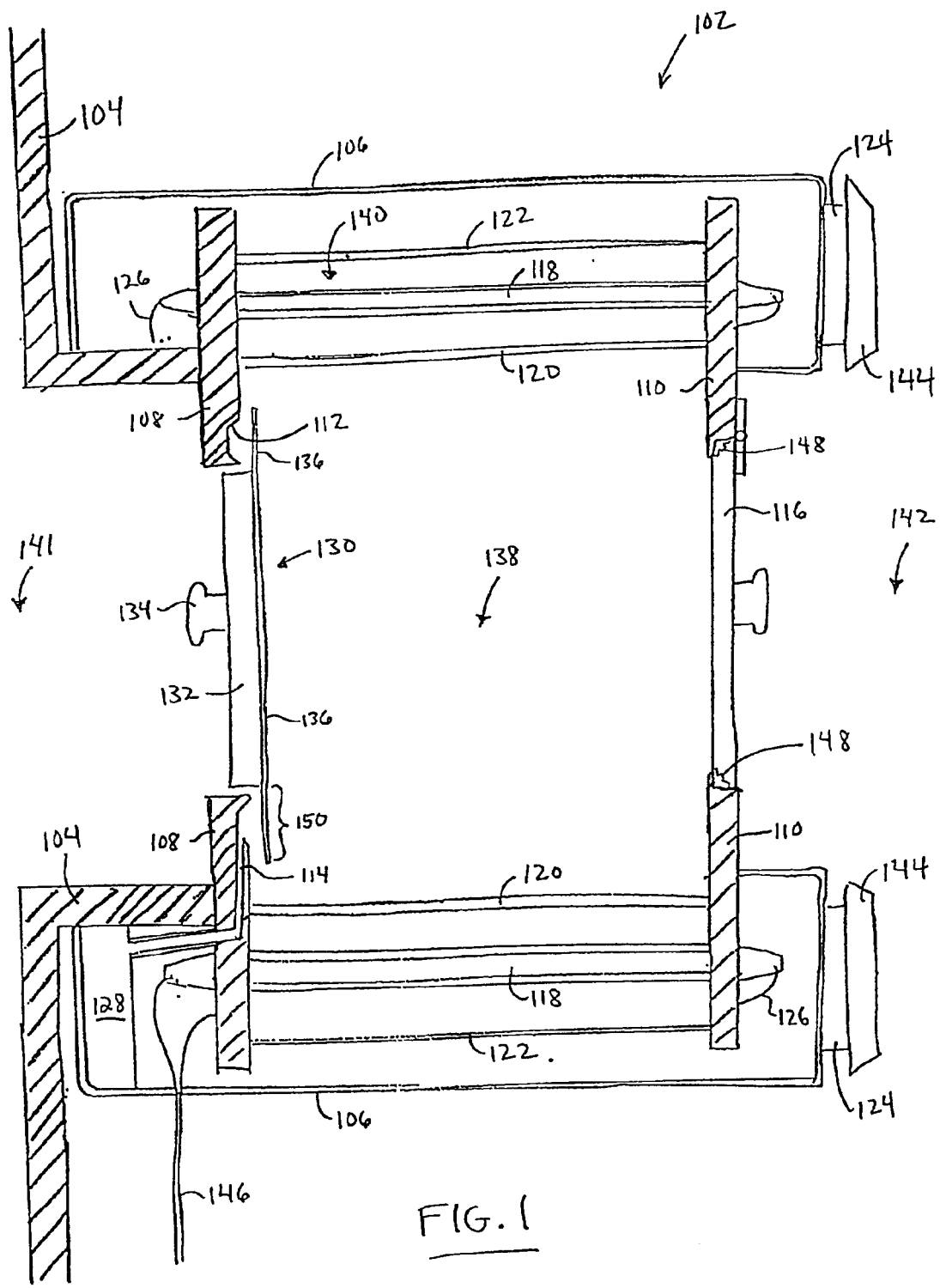
FIG. 1 is a cross sectional side view of a passthrough light treatment device integrated with a barrier isolator, wherein the passthrough light treatment device employs a vacuum-sealable hatch to effectuate a sterilized vacuum seal in accordance with one embodiment of the invention.

Referring first to FIG. 1, a cross sectional side view of a passthrough light treatment device integrated with a barrier isolator is shown, wherein the passthrough light treatment device employs a vacuum-sealable hatch to effectuate a sterilized vacuum seal in accordance with one embodiment of the invention. Shown is a passthrough device 102 and isolator walls 104 of an isolation chamber (not shown and also referred to as a barrier isolator). The passthrough device 102 includes an exterior shell 106, a first end wall 108 including a groove 112 and a vacuum port 114 (also referred to as a vacuum inlet 114) both on an interior surface of the first end wall 108, a second end wall 110, a sealed door 116 (also referred to generically as an exterior sealing device) including a seal 148, lamps 118, a transmissive barrier 120, reflectors 122, electrical leads 126, a vacuum pump 128, fans 124, fan covers 144 and a power line 146. Also shown is a vacuum-sealable hatch 130 (also referred to as a hatch assembly) including a hatch body 132 (also referred to as a hatch) having a handle 134 and a flexible sheet 136 (also referred to generically as a "flexible piece"). Also shown is a treatment chamber 138, a lamp chamber 140, a sterile environment 141 (also referred to as a substantially sterile environment) and a non-sterile environment 142.

In this embodiment, the passthrough device 102 is coupled to the isolation chamber, for example, by the first end wall 108 being rigidly attached to the isolator walls 104 adjacent to the opening to the sterile environment 141 contained within the isolation chamber. Alternatively, the passthrough device 102 is built into the structure of the isolation chamber. Thus, the passthrough device 102 is integrated with the isolation chamber either through a rigid attachment or through manufacturing. In other embodiments, the passthrough device 102 is built within a dividing wall of an isolation chamber, typically in embodiments where the isolation chamber comprises an entire room or a volume that is divided by walls.

The passthrough 102 device is a cylindrical device having a cylindrical external shell 106 that defines the passthrough device 102. Within the external shell 106, is a treatment chamber 138 which is defined as the volume within the transmissive barrier 120. The transmissive barrier 120 is a cylindrical piece of material that is transmissive to light. The volume within the passthrough device 102 that is between the exterior surface of the transmissive barrier 120 and the interior surface of the external shell 106 defines the lamp chamber 140. The lamp chamber 140 houses the lamps 118 and the reflectors 122. The lamps 118 and reflectors 122 are mounted within the lamp chamber 140. The lamps 118 provide light through the transmissive barrier 120 and treat an object placed within the treatment chamber 138. The reflectors 122 reflect light emitted away from the center of the treatment chamber 138 back toward and into the treatment chamber 138 through the transmissive barrier 120. Additionally, electrical leads 126 are coupled to the lamps 118 and to a power supply (not shown) via the power line 146. It is noted that there may be many lamps 118, for example, eight lamps, that are mounted within the volume of the external shell 106, although only two lamps 118 are shown in the cross sectional view.

These lamps 118 may be any type of lamps known in the art for light treatment. For example, the lamps may be continuous wave ultraviolet (UV) lamps that contain Mercury gas, such as those found in the passthrough device of U.S. Pat. No. 5,446,289 issued to Shodeen et al., entitled ULTRAVIOLET PASSTHROUGH STERILIZATION DEVICE (hereinafter referred to as the '289 patent) uses continuous ultraviolet light (UV) to treat the non-sterile object within a treatment chamber.

Preferably, the lamps 118 comprise Xenon flashlamps that produce pulsed polychromatic light as further described in U.S. patent application Ser. No. 09/580,361, filed May 26, 2000, of Cooper, et al., entitled BROAD-SPECTRUM PULSED LIGHT PASSTHROUGH STERILIZATION DEVICE, now abandoned, which is incorporated herein by reference. Pulsed polychromatic light may be referred to as broad-spectrum pulsed light (BSPL). Such pulsed polychromatic light is in the form of short duration, high intensity pulses of polychromatic light in a broad spectrum. For example, the pulsed polychromatic light should include light within a range of 170 nm to 2600 nm with at least 1% (preferably at least 10% and more preferably at least 50%) of an energy density concentrated at wavelengths within a range of 200 nm to 320 nm. In one example using pulsed polychromatic light, the object is illuminated by at least one, preferably two and most preferably three short duration (e.g., less than about 100 ms, preferably about 0.3 ms) pulses of high-intensity (e.g., 0.01 J/cm$^2$ to 50 J/cm$^2$, e.g., 0.05 J/cm$^2$ to 1.0 J/cm$^2$, measured at the surface of the object) incoherent polychromatic light in a broad spectrum (e.g., 170 nm to 2600 nm; i.e., $1.8\times10^{15}$ Hz to $1.2\times10^{14}$ Hz). However, such light may be within any subset of the range of 170 nm to 2600 nm, e.g., the energy density of the pulsed light may be concentrated within wavelengths between 170 nm and 1000 nm, between 200 nm and 500 nm, or between 200 nm and 300 nm, for example. This light is commonly produced by Xenon gas flashlamps. As a result of such illumination, microorganisms on the surface of the object, on the inner surfaces of the treatment chamber, and contained within the air within the treatment chamber are effectively deactivated to a level of 6 to 7 logs reduction (i.e. a microbial reduction level that is commonly accepted as sterilization). Thus, in passthrough devices using pulsed polychromatic light, the treatment chamber 138 is referred to as a "sterilization chamber". In this embodiment, fans 124 are included with fan covers 144 in order to provide cooling air through vents (not shown) to the lamps 118. The fan covers 144 block light from escaping the exterior shell 106.

Several other apparatus designed to provide high-intensity, short duration pulsed incoherent polychromatic light in a broad-spectrum are described, for example, in U.S. Pat. No. 4,871,559, issued Oct. 3, 1989; U.S. Pat. No. 4,910,942, issued Mar. 27, 1990; U.S. Pat. No. 5,034,235, issued Jul. 23, 1991; U.S. Pat. No. 5,489,442, issued Feb. 6, 1996; U.S. Pat. No. 5,768,853, issued Jun. 23, 1998; U.S. Pat. No. 5,786,598, issued Jul. 28, 1998; and U.S. Pat. No. 5,900,211, issued May 4, 1999, all of which are assigned to PurePulse Technologies, Inc. of San Diego, Calif., and each of which is hereby incorporated by reference in its entirety.

At both ends of the treatment chamber 138 are the first end wall 108 and the second end wall 110. These end walls are generally circular walls that seal against the respective circular ends of the transmissive barrier 120. Thus, the transmissive barrier 120 extends the length of the external shell 106 and terminates at the first end wall 108 and the second end wall 110. Each of the first end wall 108 and the second end wall 110 includes a respective opening. Ideally, these openings are circular, as viewed looking into the openings. For example, the opening in the second end wall 110 allows access into the treatment chamber 138 from the non-sterile environment 142, while the opening in the first end wall 108 allows access into the treatment chamber 138 from the sterile environment 141.

In the context of passthrough treatment devices, at least one of the two openings should be sealed at all times to prevent the free flow of microorganisms between the non-sterile environment 142 and the sterile environment 141. During use, the treatment chamber 138 of a passthrough device 102 should be sealed during the light treatment process so that the contaminants in the treatment chamber 138 do not escape into the sterile environment 141 prior to the light treatment and also so that contaminants from the non-sterile environment 142 do not infiltrate the air within the treatment chamber 138 after the light treatment is complete. Thus, each of the openings at the first end wall 108 and the second end wall 110 must be made sealable from both the sterile environment 141 and the non-sterile environment 142 in order for the passthrough device 102 to correctly operate.

In this embodiment, a sealed door 116 is used to seal the opening of the second end wall 110. Thus, the sealed door 116 seals the opening of the second end wall 110. The seal 148 of the sealed door 116 contacts a surface of the second end wall 110 to effectuate the seal. As such, the seal 148 is a molded seal or gasket that is preferably annularly shaped. The seal is effectuated when the sealed door 116 is brought into a closed position and mechanical pressure is applied to hold the sealed door 116 within the opening of the second end wall 110. The sealed door 116 may be similar to sealed door designs found in known passthrough devices. For example, conventional approaches use mechanical sealed door designs to seal the treatment chamber 138 of the passthrough device 102 from the sterile environment 141 and the non-sterile environment 142. Such sealed door designs have an open position and a closed position. In the open position, an operator may access the treatment chamber 138 to place an object therein or to remove an object. In the closed position, the treatment chamber 138 is sealed from the respective environment.

One example of a sealed door system for a treatment chamber of a conventional passthrough device is described in the '289 patent. Another example of a sealed door system (not illustrated herein) is described in the above-mentioned U.S. patent application Ser. No. 09/580,361 (which was previously incorporated herein by reference), which uses a complex mechanical combination of interlocking flanged doors mechanically held together and including precisely molded annular seals or gaskets. Both examples involve sealed doors that are held within the opening with mechanical pressure and seals that are precisely formed.

According to one embodiment of the invention, the opening of the first end wall 108 is made sealable with the vacuum-sealable hatch 130. The vacuum-sealable hatch 130 includes the hatch body 132, the handle 134, and the flexible sheet 136 attached to the interior surface of the hatch body 132. The vacuum-sealable hatch 130 is an alternative to a mechanically sealed door design and according to one embodiment, is vacuum sealed within the opening of the first end wall 108. In other words, the vacuum-sealable hatch is vacuum sealed within an opening to the treatment chamber 138.

As such, according to this embodiment of the invention, the vacuum-sealable hatch 130 is employed to effectively seal the treatment chamber 138 from an outside environment, e.g., the sterile environment 141. The hatch body 132 is designed such that at least a portion of an exterior dimension of the hatch body 132 generally conforms to the geometric shape of the interior of the opening of the first end wall 108. However, the exterior dimension of the hatch body 132 is slightly smaller than the opening so that at least a portion of the hatch body 132 will fit within the opening. In this embodiment, the entire hatch body 132 is designed to fit within the opening. The flexible sheet 136 is attached on one side of the hatch body 132, but is designed to overlap the hatch body 132 by a predetermined distance, such that the flexible sheet 139, if not flexible, would not fit within the opening of the first end wall 108. The overlapping portion of the flexible sheet 136 is referred to as a periphery portion 150 of the flexible sheet 136. Advantageously, since the flexible sheet 136 is "flexible", the periphery portion 150 bends easily; thus, the vacuum-sealable hatch 130 can be pushed through the opening. In operation, the vacuum-sealable hatch 130 is pushed through the opening of the first end wall 108 with the flexible sheet 136 entering the opening first before the hatch body 132. Once the flexible sheet 136 is pushed through the opening, the periphery portion 150 returns to its normal flat state, since the interior volume of the treatment chamber 138 is larger than the opening. Next, the vacuum-sealable hatch 130 is positioned within the treatment chamber 138 such that the hatch body 132 is within the opening of the first end wall 108 and the periphery portion 150 of the flexible sheet 136 is flush against an inner surface of the first end wall 108 (i.e., flush against an inner surface of the treatment chamber 138).

The inner surface of the first end wall 108 includes the groove 112 over which the periphery portion 150 of the flexible sheet 136 is positioned. The groove 112 contains a vacuum port 114 (or vent or inlet) coupled to the vacuum pump 128 that evacuates air from the groove 112 and thereby tightly pulls the periphery portion 150 of the flexible sheet 136 into the groove 112, thereby conforming the periphery portion 136 to the shape of the groove 112; thus, sealing the treatment chamber 138 from the sterile environment 141. It is noted that the interior surface of the first end wall 108 containing the groove and the vacuum ports is referred to as a "seating region", which will be sealed with a corresponding seating portion of the periphery portion.

It is also noted that in some embodiments, a pinch valve or switch in the path of the vacuum port 114 is utilized to prevent air-borne microorganisms within the air supply of the vacuum pump 128 or within the vacuum port 114 from being re-introduced into the treatment chamber 138 once treated. For example, such a pinch valve would only allow for air within the vacuum port 114 to move in one direction, e.g., away from the groove 112. Thus, any microorganisms pulled within the vacuum pump 128 would not be re-introduced upon deactivating the vacuum seal. Alternatively, a switch valve could be activated once the vacuum pump is to be disengaged to a clean air source (e.g., a sterile air source), such that any air drawing back into the treatment chamber 138 will be from the clean air source, not from within the vacuum pump 128.

Advantageously, in this embodiment, the flexible sheet 136 is transmissive to the light emitted from the lamps 118. For example, the flexible sheet 136 may be a thin flexible sheet comprised of polyethylene or polypropylene. As such, the flexible sheet 136 will transmit at least 50%, preferably at least 70–85% of the light energy through the flexible sheet 136 to the surface underneath. Thus, advantageously, the light is able to deactivate organisms under the surface of the flexible sheet 136, for example, within the groove 112 in the first end wall 108, which is described in more detail with reference to FIGS. 2A through 2H. Furthermore, the flexible sheet 136 is designed to be thin enough to easily bend and flex allowing the flexible sheet 136 to fit into the opening, yet be elastic enough or rigid enough to generally return to a flat position without any pressure applied to the flexible sheet 136.

Similar to the flexible sheet 136, the transmissive barrier 120 and the transmissive shelf (not shown) will also transmit light from the lamps 118 onto the object to be sterilized. Typically, the transmissive barrier 120 and the transmissive shelf are comprised of quartz, sapphire, or another suitable material that is at least about 1%, preferably at least about 10%, more preferably at least about 50% and most preferably at least about 70–85% the light produced by the lamps 118.

Additionally, the hatch body 132 of the vacuum-sealable hatch 130 is preferably opaque, or non-transmissive to the light generated within the treatment chamber 138. This effectively prevents light from within the treatment chamber 138 from escaping into the sterile environment 141. Thus, the treatment chamber 138 is essentially "light-tight", except at the perimeter of the hatch body 132 if there is any spacing between an outer edge of the hatch body 132 and an inner edge of the opening in the treatment chamber 216. Note that several embodiments of the hatch assembly 204, described below, are designed to reduce or eliminate escape of light from between the outer edge of the hatch body 132 and the inner edge of the opening to the treatment chamber 138. Furthermore, in some embodiments, the inner surface (shown in FIGS. 2A–2H) of the hatch body 132, i.e., the surface directly underneath the flexible sheet 136 and facing the treatment chamber 138, is a reflective inner surface, such that light from within the treatment chamber 138 is reflected back towards the interior of the treatment chamber 138 where the item to be treated with light is located. Since the flexible sheet 136 is transmissive to light, the light will advantageously go through the flexible sheet 136 and reflect off of the inner reflective surface back through the flexible sheet 136 into the treatment chamber 138.

Note that in the embodiment shown in FIG. 1, only one vacuum-sealable hatch 130 is used in the first end wall 108; however, in other embodiments, the opening of the second end wall 110 may also use a similar vacuum-sealable hatch.

It is also noted that the passthrough device utilizing the hatch assembly 204 of this and other embodiments may use any means of light treatment, such as continuous wave ultraviolet (UV) or pulsed polychromatic light, such as described herein and within U.S. patent application Ser. No. 09/580,361. In the case of a pulsed light passthrough device, the treatment chamber 138 is referred to as a "sterilization chamber", since the pulsed light is capable a microbial deactivation of 6–7 logs reduction (which is commonly accepted as sterilization). Furthermore, this and other embodiments of the vacuum-sealable hatch 130 also apply to treatment chambers generally, with a passthrough chamber being one specific type of treatment chamber. Furthermore, this and other embodiments of the vacuum-sealable hatch 130 also apply to treatment chambers that do not use light, such as chemical or heat treatment chambers; however, an important feature of the vacuum-sealable hatch 130 of this embodiment is that light may treat the surfaces that the periphery portion 150 of the flexible sheet 136 covers, whereas chemical and/or heat treatments may not adequately treat those surfaces.

Referring next to FIGS. 2A through 2H, lengthwise cross sectional views of the vacuum-sealable hatch 130 of FIG. 1 are shown in operation at the various stages during use of an embodiment of the passthrough device 102 of FIG. 1. In addition, while referring to FIGS. 2A–2H, concurrent reference will be made to FIG. 3, which illustrates a flowchart 300 of the steps performed for vacuum sealing a non-sterile object within a treatment chamber of the passthrough device of FIGS. 2A through 2H, treating the non-sterile object with light, and passing it into a sterile environment.

Shown in FIGS. 2A through 2H is one embodiment of a passthrough device including the treatment chamber 138, the transmissive barrier 120, the first end wall 108 including the groove 112 and the vacuum port 114 (also referred to as a "vacuum inlet"), the second end wall 110, the sealed door 116 having a reflective inner surface referred to as a second reflective inner surface 204, lamps 118, the sterile environment 141 (also referred to as the substantially sterile environment), and the non-sterile environment 142. Also shown are the vacuum-sealable hatch 130 including the hatch body 132 having the handle 134 and a first reflective inner surface 202 and a flexible sheet 136 (also referred to generically as a "flexible piece") attached to the inner surface of the hatch body 132 over the first reflective inner surface 202 of the hatch body 132. The periphery portion 150 of the flexible sheet 136 overlaps the hatch body 132. Also shown is an object 206 to be treated within the treatment chamber 138 of the passthrough device and isolation chamber walls 104.

Figure 2A:
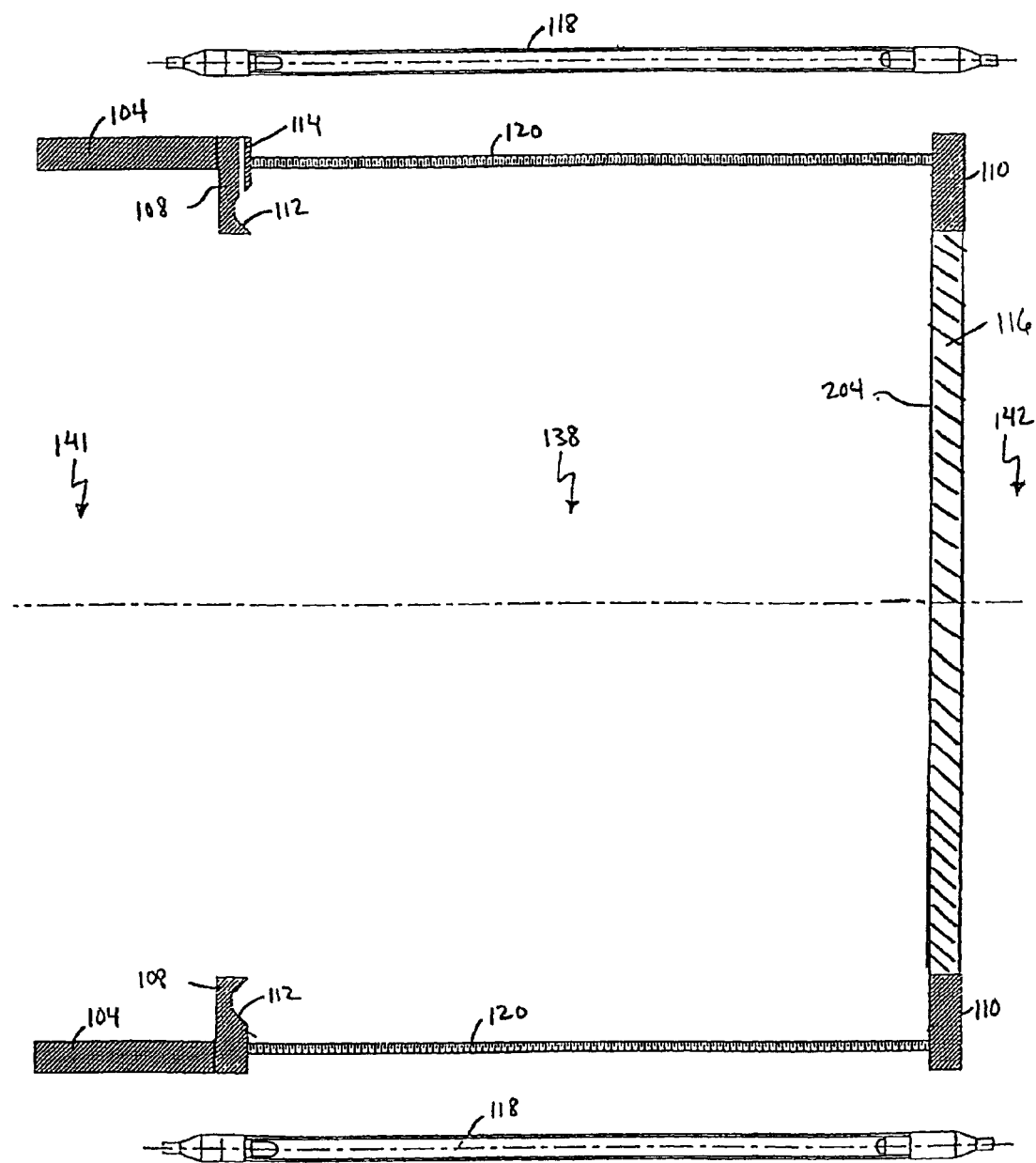

First, referring to FIG. 2A, and in the context of FIG. 1, the passthrough device includes an external shell (not shown) which defines the passthrough device, and thus, the components of the passthrough device shown are contained within the external shell of FIG. 1. The volume within the transmissive barrier 120 defines the treatment chamber 138 and also includes a transmissive shelf (not shown) that supports an object within the treatment chamber 138. The transmissive barrier 120 may be cylindrically shaped, shown as a cross sectional lengthwise view, although it may be other shapes as described above. The first end wall 108 and the second end wall 110 sealingly engage the ends of the transmissive barrier 120 around the perimeter of the transmissive barrier 120. For example, the first end wall 108 and the second end wall 110 may be sealed to the ends of the transmissive barrier 120 using seals, adhesive, or other mechanical means of connecting the end walls to the ends of the transmissive barrier 120. Additionally, the first end wall 108 and second end wall 110, respectively, have openings that are accessible from the sterile environment 141 and the non-sterile environment 142, respectively. These openings are typically circular openings within circular end walls that sealingly engage the ends of the cylindrical transmissive barrier 120. These openings may be sealed with conventional sealed door systems, as described above, or in this embodiment, with a vacuum-sealable hatch 130.

In an alternate embodiment, there may be only one opening to the treatment chamber 138; thus, the treatment chamber 138 is used as a rapid transfer port or a treatment device that an object is placed into, sterilized therein, and then removed from the treatment chamber 138 into an outside environment, which may be a sterile environment or a non-sterile environment, for example.

As shown, only one of the two openings is shown as being sealed with the vacuum-sealable hatch 130, while the opening to the non-sterile environment 142 is sealed with the sealed door 116. Alternatively, the sealed door 116 may comprise another vacuum-sealable hatch 130 or other means of sealing the opening in the treatment chamber 138. Furthermore, in embodiments including only one opening to the treatment chamber 138, the sealed door 116 may simply be an end wall that does not have an opening formed therein, such that the passthrough device acts a rapid transfer port (RTP) instead of a passthrough device.

Also illustrated are two lamps 118, for example Xenon gas flashlamps or Mercury gas ultraviolet lamps, depending on whether the passthrough device is a UV passthrough device as shown in the '289 patent or a pulsed polychromatic light passthrough device as shown in U.S. patent application Ser. No. 09/580,361, that are positioned about the outer surfaces of the transmissive barrier 120. Preferably, in the case that the transmissive barrier 120 is cylindrically shaped, the lamps 118 radially surround the transmissive barrier 120, for example, there may be six to eight lamps 118 equally spread out around the perimeter of the transmissive barrier 120. Note that since FIGS. 2A through 2H are cross sectional views, only two lamps 118 are shown. As described above, the transmissive barrier 120 is designed to transmit the light emitted from the lamps 118. For example, using Xenon flashlamps emitting light having a wavelength of 170 nm to 2600 nm, the transmissive barrier 120 transmits at least 50%, and preferably at least 70%, and most preferably at least 85% of the light from the lamps 118. Also, in the Xenon lamp embodiment, cooling features, such as fans, are needed to cool the Xenon flashlamps during operation.

Also shown is the first end wall 108 illustrated as sealingly engaging the sterile environment 141 end of the transmissive barrier 120 and including an opening formed within. The opening allows an operator to access the treatment chamber 138 from the sterile environment 316. Furthermore, the first end wall 108 has the groove 112 (also referred to as an annular groove or channel) formed at the inner surface of the first end wall 108 proximate to (i.e. near) the periphery of the opening of the first end wall 108. In this embodiment, the groove 112 is a trapezoidal type shape set into the thickness of the inner surface of the first end wall 108. The groove 112 is typically an annular groove that extends completely around the inner surface of the first end wall 108 and proximate to the periphery of the opening of the first end wall 108, similar to a ring around the inner surface of the first end wall 108. For example, if the transmissive barrier 120 was cylindrically shaped, the first end wall 108 would be generally circular in shape and the opening to the treatment chamber 138 might also be circular in shape; thus, the groove 112 would extend as an annular groove or channel around the periphery, i.e. the circumference, of the first end wall 108.

Furthermore, at or near the base of the groove 112 or channel, a vacuum port 114 extends from the groove 108 and is coupled to a vacuum pump (shown in FIG. 1). The vacuum port 114 may be many vacuum ports, acting as small pipes or lines, evenly spaced about the groove 112 around the circumference of the first end wall 108 (see FIG. 10) or it may be one annular vacuum port 114 along the entire perimeter of the groove 112 that provides a vent for every portion of the groove 112. In operation, the vacuum pump pulls air from through the vacuum port 114 to create a vacuum seal at the groove 112 with materials that are placed thereagainst, which is described more fully below. Thus, the inner surface of the first end wall 108, including the groove 112 and vacuum port/s 114 forms a "vacuum sterilizable sealing surface" since it is the surface where the seal is formed and is also a surface that is treated with the sterilizing light.

In other embodiments, it may not be necessary to have a groove 112 formed in the inner surface of the first end wall 108. For example, a vacuum port 114 that extends annularly around the inner surface of the first end wall 108 may sufficiently pull the periphery portion 150 of the flexible sheet 136 against the inner surface of the first end wall 108 without pulling the periphery portion 150 into a groove 112. Thus, in this embodiment, the "vacuum sterilizable sealing surface" is the inner surface of the first end wall 108 that includes the vacuum port/s 114. Furthermore, the groove 112 and/or vacuum port 114 may be located at an outer surface of the first end wall 108 or within the thickness of the first end wall at its opening.

Figure 3:
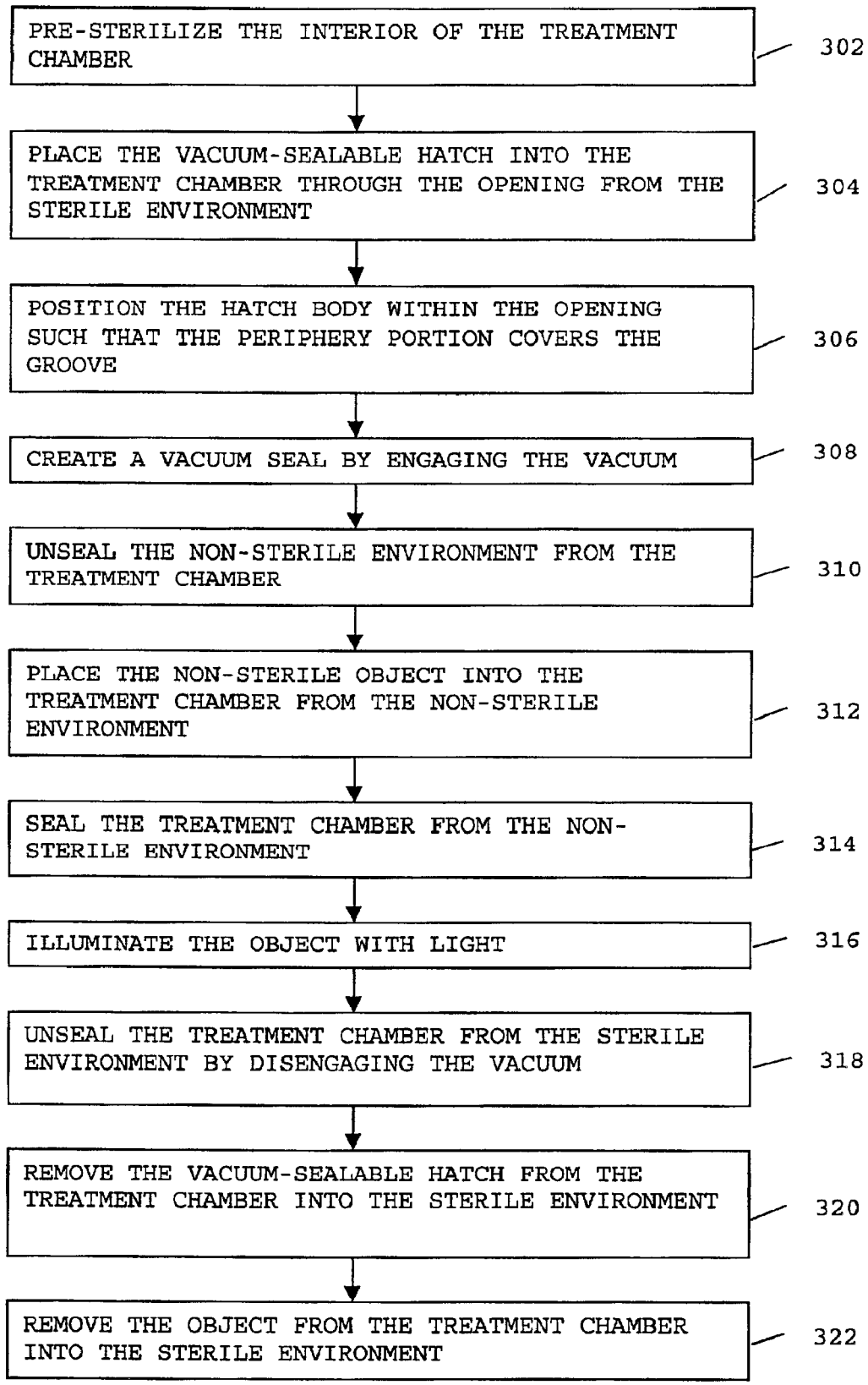
FIG. 3 is a flowchart of the steps performed in FIGS. 2A–2H for sealing an object within the passthrough treatment device, such as the passthrough light treatment device of FIG. 1, treating the object, and passing the object into a sterile environment.

While operating the passthrough device, initially, with the sealed door 116 sealing the treatment chamber 138 from the non-sterile environment 142, the entire treatment chamber 138, including the groove 112 and the vacuum ports 114 and with the vacuum-sealable hatch 130 removed, is pre-sterilized (Step 302 of FIG. 3). Such pre-sterilization may also be performed using chemicals, such as hydrogen peroxide, and acts to completely sterilize the interior of the treatment chamber 138 at the initial setup, since light does not reach into the vacuum port 114 during use.

Figure 2B:
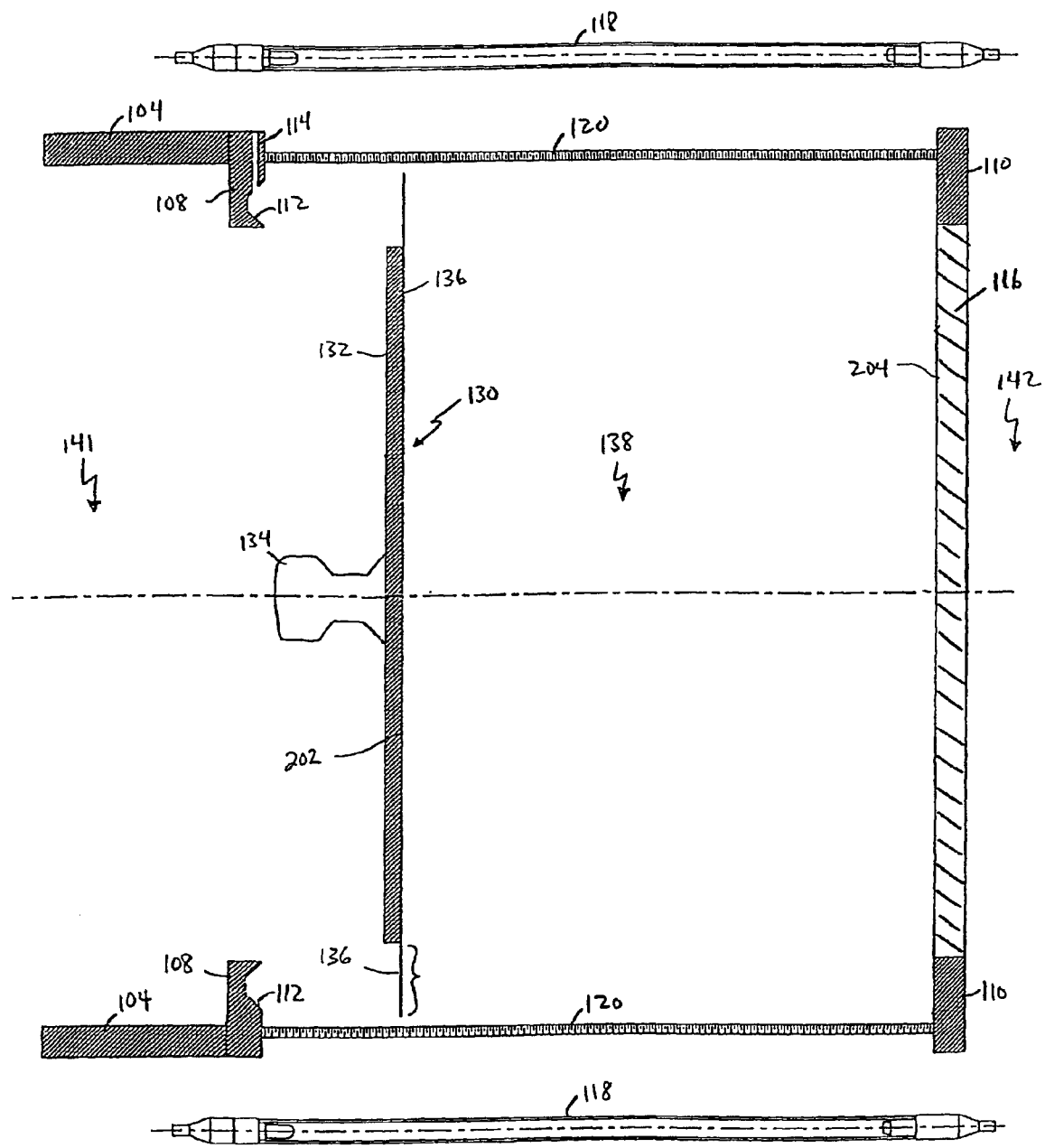

Referring next to FIG. 2B, after the initial setup sterilization is complete, the vacuum-sealable hatch 130 is placed through the opening in the first end wall 108 from the sterile environment 138 (Step 304 of FIG. 3). Note that the hatch body 132 that generally conforms to the geometric shape of the opening and is sized slightly smaller than the opening such that the hatch body 132 will fit through the opening. The periphery portion 150 of the flexible sheet 136 that overlaps the external dimensions of the hatch body 132 is flexible enough to simply fold over while being inserted through the opening of the treatment chamber 138. Once the vacuum-sealable hatch 130 is within the treatment chamber 138, the periphery portion 150 of the flexible sheet 136 returns to its original position, instead of staying folded or bent. Thus, the flexible sheet 136 is elastic enough to allow bending, yet still able to return to its original position. The flexible sheet 136 is a thin sheet typically comprised of light transmissive polyethylene, polypropylene, perfluoro ethylene propylene (FEP), perfluoro alkoxy alkane (PFA) or ethylene vinyl acetate (EVA). It is typically attached to the hatch body 132 with adhesives.

In preferred embodiments, the flexible sheet is light transmissive to the light produced by the lamps 118. In alternative embodiments, the flexible sheet 136 is not transmissive to sterilizing light; however, in such embodiments, the area underneath the flexible sheet 136 will not be effectively treated. On the other hand, this embodiment effectively blocks light from escaping into the sterile environment 141 through the spacing between the hatch body 132 and the opening of the first end wall 108.

Furthermore, the flexible sheet 136 may not be a full sheet of flexible material but rather may comprise only the periphery portion 150 and just enough material to attach the flexible sheet 136 to the first reflective inner surface 202 of the hatch body 132 at or near the periphery edges of the hatch body 132. Thus, the flexible sheet 136 takes the form of a sheet of flexible, light transmissive material (e.g. polypropylene or polyethylene) that has a circular shape cut out of the center of the flexible sheet 136; thus, resembling a ring of the periphery portion 136. As such, this embodiment is referred to as a flexible skirt (see FIG. 5B) which is also referred to generically as a flexible piece. The circular shape cut out of the flexible sheet 136 would be slightly smaller than the external dimensions of the hatch body 132 so that the flexible material can be attached to the first reflective inner surface 202. Again, it is preferable that the flexible sheet 136 is transmissive to sterilizing light.

Figure 2C:
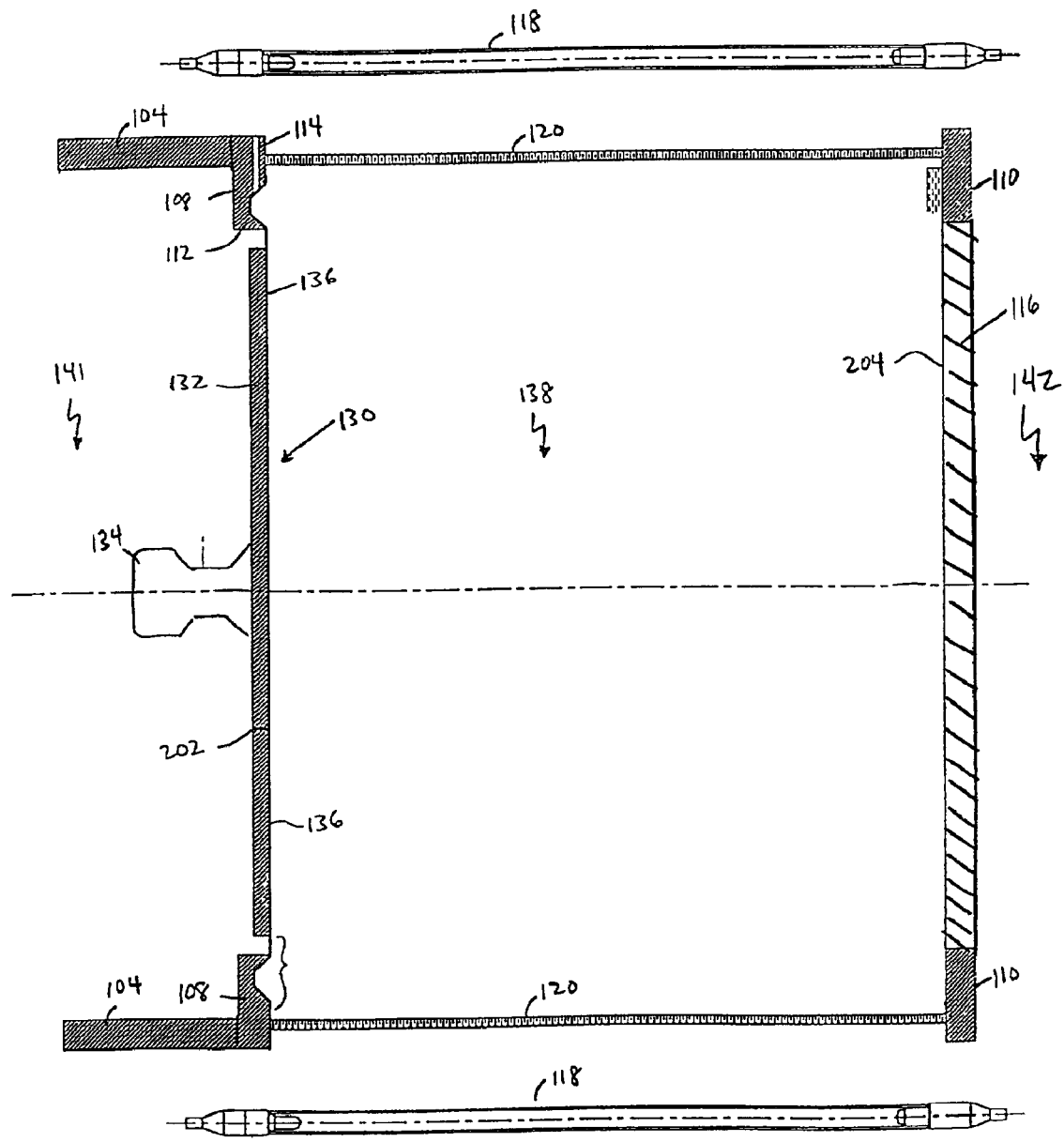

Next, as illustrated in FIG. 2C, the vacuum-sealable hatch 130 is positioned such that the hatch body 132 is within the opening of the first end wall 108 such that the periphery portion 150 of the flexible sheet 136 entirely covers (i.e. is positioned flush against) the groove 112 and the hatch body 132 is within the space formed by the opening (Step 306 of FIG. 3). As will be further described, a "seating portion" of the periphery portion 150 is positioned to seal with the groove 112 and the vacuum ports 114 of the first end wall 108. The groove and the vacuum ports may be referred to as a "seating region" of the first end wall 108. The vacuum pump is then engaged (Step 308 of FIG. 3), which draws air through the vacuum port 114 and which pulls the periphery portion 150 of the flexible sheet 136 snugly into the groove 112 so as to lock the flexible sheet 136, and thus, the hatch body 132, into place. Thus, a vacuum seal is formed between the periphery portion 150 of the flexible sheet 136 and vacuum port/s 114 within the annular groove 112 extending completely around the opening of the first end wall 108. The vacuum pump is any such pump as known in the art. Thus, advantageously, the treatment chamber 138 is effectively sealed from the sterile environment 141 by the vacuum-sealable hatch 130, without the use of complex structural door designs or precisely cut or molded seals.

Advantageously, several problems associated with some types of sealed door designs are eliminated, for example, precisely molded or cut seals that are difficult to replace are not required. The flexible sheet 136 of this embodiment is easy to manufacture since the dimensions of the flexible sheet 136 are not required to be exact or precise, as in the case with typical sealed door systems, but only as precise to ensure that the periphery portion 150 adequately overlaps the hatch body 132 to cover the groove 112 and the vacuum ports 114. Also, the flexible sheet 136 should not be cut so big such that the periphery portion 150 of the flexible sheet 136 contacts the inner surface of the transmissive barrier 120. The flexible sheet 136 is typically held in place on the hatch body 132 with the use of adhesives, for example.

Further advantageously, the flexible sheet 136 is designed to be disposable, such that after a predetermined number of uses, the flexible sheet 136 is simply removed from the hatch body 132 and replaced with a new flexible sheet 136. This is due to the fact that repeated exposure of the flexible sheet 136 to UV light or pulsed light could physically degrade the flexible sheet 136.

Another problem avoided with this embodiment of the present invention is the problem of physically warped door components (such as the door arm, hinges, or locking devices) that do not place an even amount of pressure against the seals of the door and the contact area of the opening. In contrast, the vacuum seal formed with the vacuum-sealable hatch 130 and the vacuum port/s 114 and groove 112 creates the same sealing properties each time, depending on the reliability of the vacuum pump and the specific characteristics and thickness of the flexible sheet 136. The physical warping of the door components is not a concern in the vacuum-sealable hatch design as compared to the prior art sealed door systems. For example, even if the hatch body 132 became warped or bent, the periphery portion 150 of the flexible sheet 136 is designed to be "flexible", so that when the vacuum pump is engaged, the flexible sheet 136 still conforms to the interior of the groove, regardless of imperfections in the structure of the hatch body 132.

It is also noted that in embodiments that do not use a groove 112, a single vacuum port 114 extending annularly about the inner surface of the first end wall 108, or several intermittent vacuum ports 114 located variously about the perimeter of the opening and, proximate to the opening is used. The vacuum seal is then formed between the inner surface of the first end wall 108 at the vacuum port/s 114 and the periphery portion 150 of the flexible sheet 136. This may provide an adequate vacuum seal; however, a groove 112 is preferable since the periphery portion 150 will be pulled into the groove 112 at the vacuum port 114 which will create a more effective locking of the vacuum-sealable hatch 130 within the opening and make it more difficult for microorganisms to somehow get underneath the seal and into the sterile environment 142. Note, however, that since the flexible sheet 136 is transmissive to the sterilizing light, and microorganisms that somehow get underneath the periphery portion 150 of the flexible sheet 136 will be deactivated during the light treatment process. Thus, the interior surface of the first end wall 108 underneath the periphery portion 150 may be referred to as a sterilizable sealing surface.

It is noted also that the embodiments using a groove 112, the groove 112 is trapezoidally shaped. This provides an interior dimension of the groove such that there is no shading within the groove, where microorganisms can escape the light treatment. For example, if the cross sectional shape of the groove 112 were that of a square, microorganisms located in the corners of the square may escape the light treatment, i.e. the corners may be shaded. The trapezoidal shape allows light to easily reach all portions within the groove 112. Alternatively, the groove may have an elongated semicircular cross section such that the ends of the semicircle are tapered to form a gradual change from the semicircle shape to the surface of the first end wall 108.

Figure 2D:
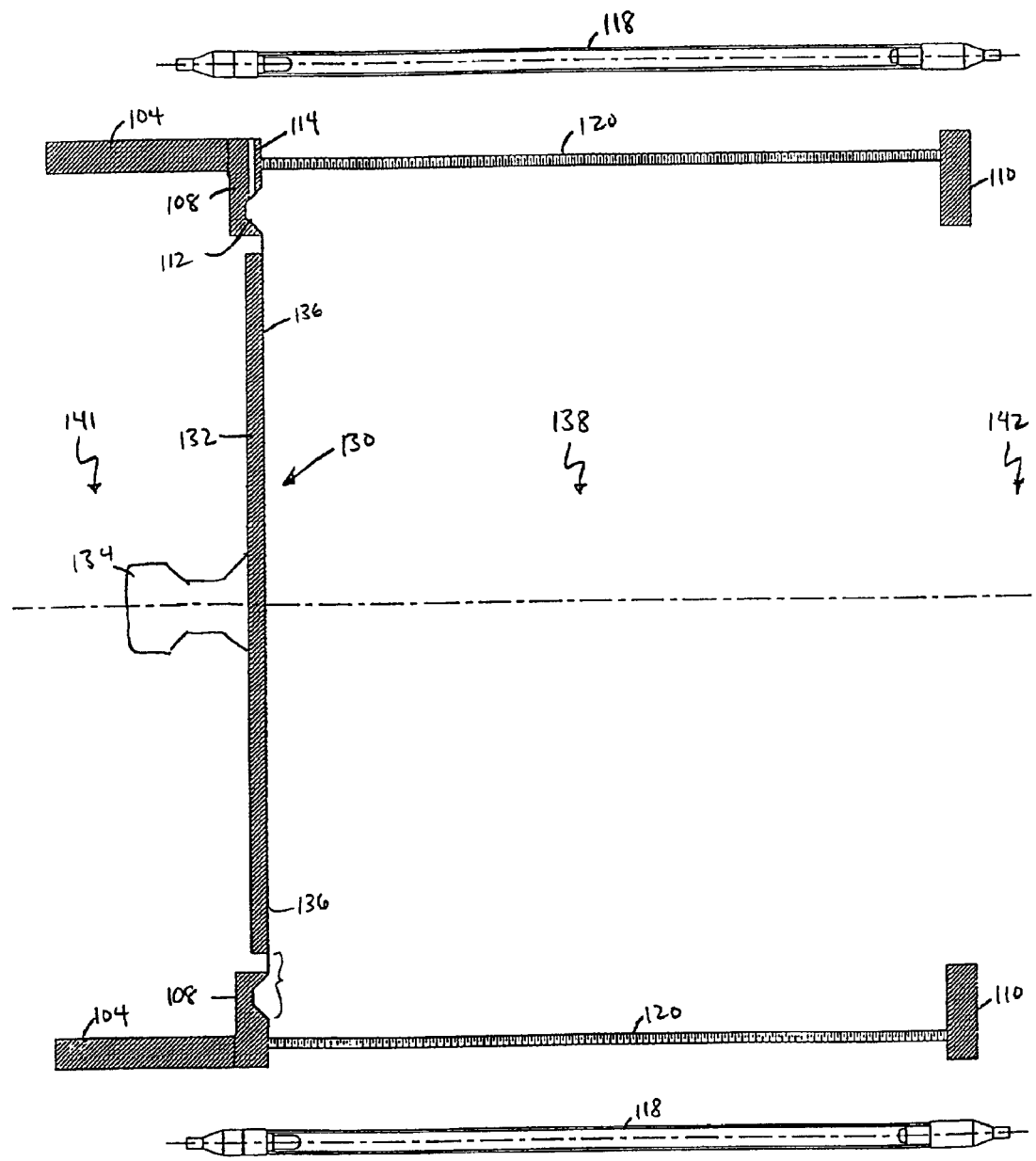

Referring next to FIG. 2D, once the vacuum seal is formed between the groove 112 at the vacuum port 114 and the periphery portion 150 of the flexible sheet 136, the non-sterile environment 142 is "unsealed" from the treatment chamber 138 by unsealing or opening the sealed door 116 from the second end wall 110 (Step 310 of FIG. 3). Again, the sealed door 116 may be another vacuum-sealable hatch or other sealing mechanism.

Figure 2E:
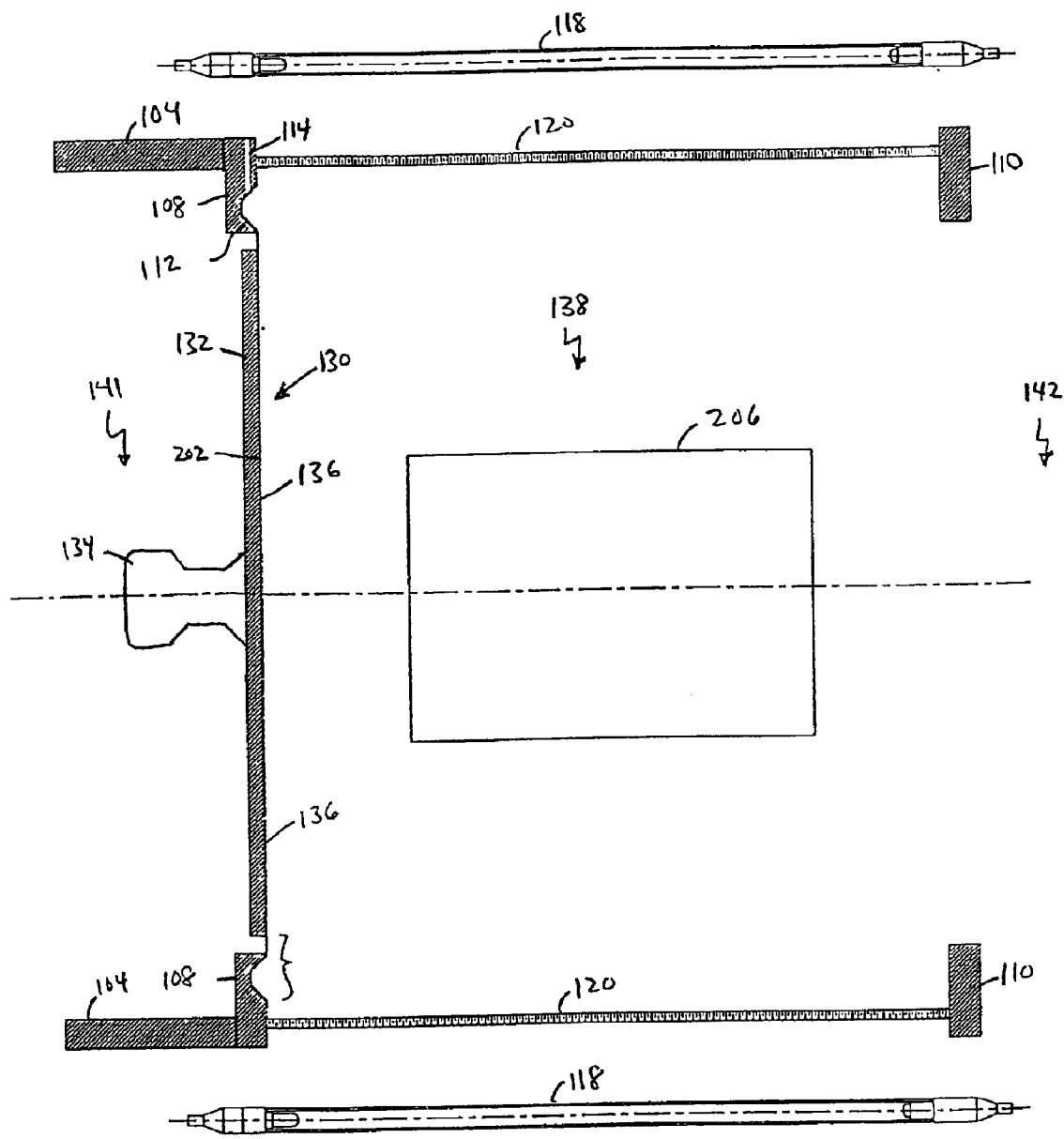
Figure 2F:
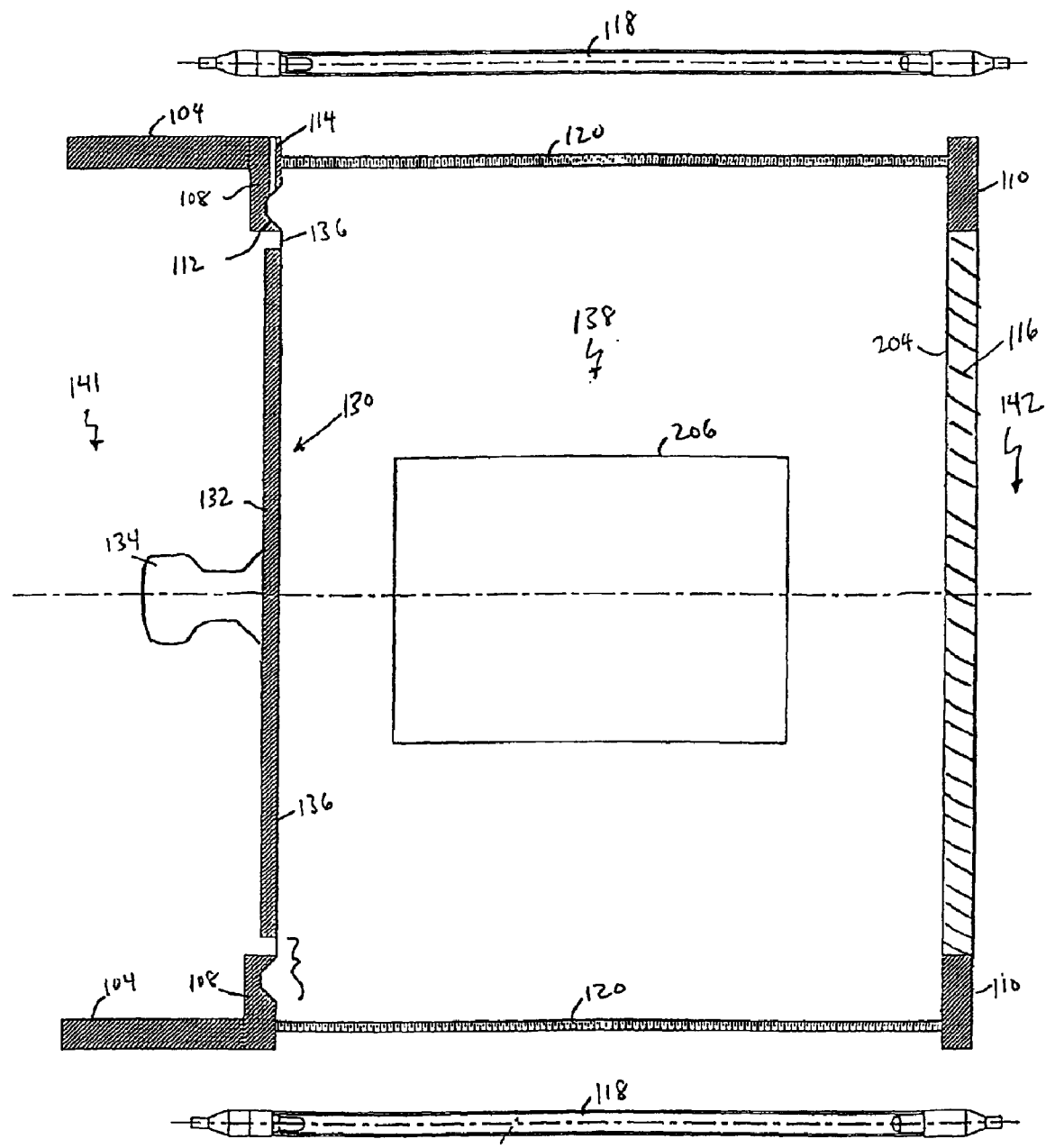
Figure 26:
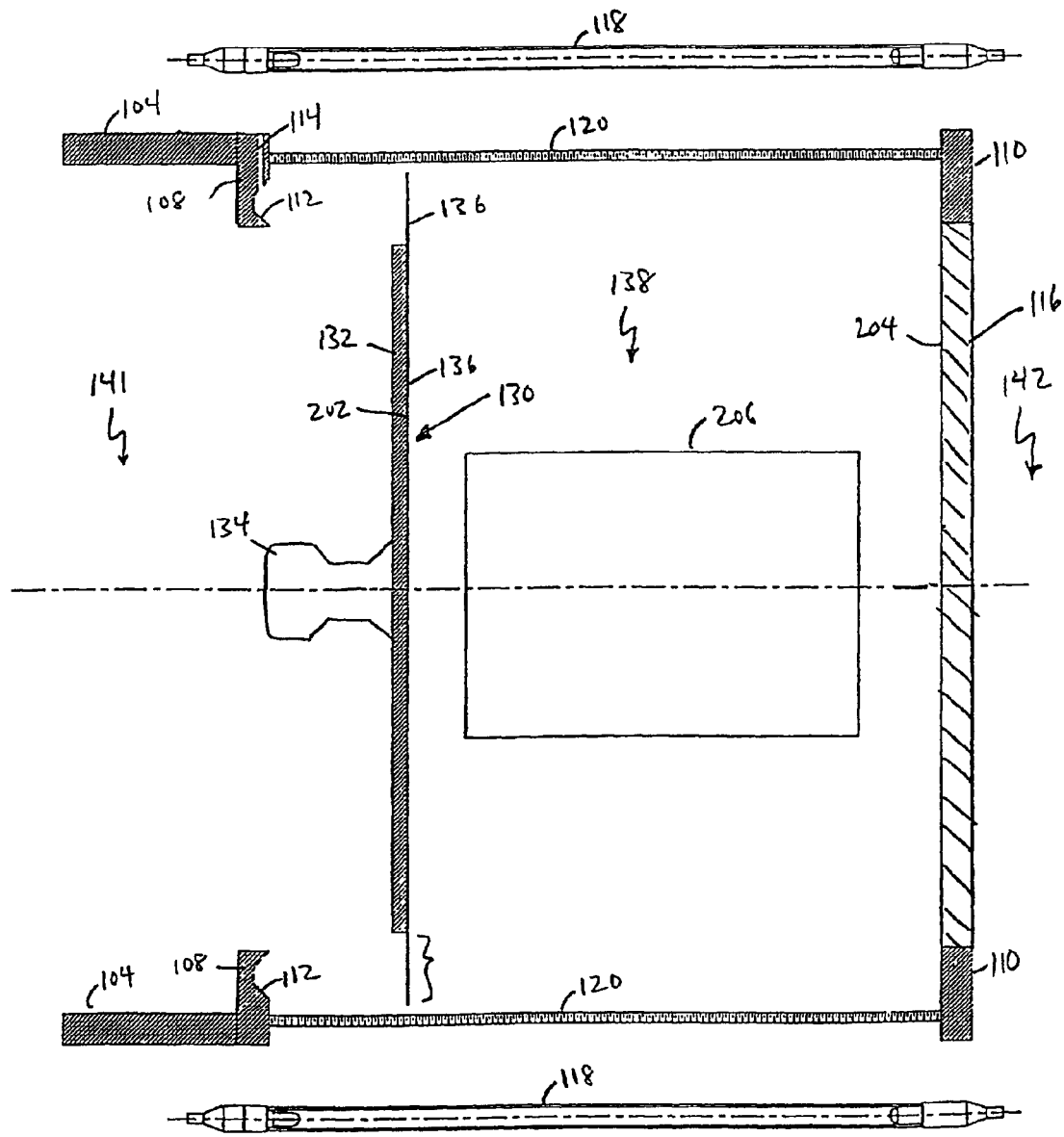

Referring next to FIG. 2E, the object 206 to be treated is then placed from the non-sterile environment 142 into the treatment chamber 138 to be treated (Step 312 of FIG. 3). Thus, the non-sterile object 206 and air-borne microorganisms are introduced into the treatment chamber 138. Note that the vacuum-sealable hatch 130 remains sealed at the vacuum port 114. Next, as illustrated in FIG. 2F, the sealed door 116 is resealed to the second end wall 110; thus, sealing the treatment chamber 138 from the non-sterile environment 142 (Step 314 of FIG. 3). Now, the treatment chamber 138 is sealed from both the non-sterile environment 142 and the sterile environment 141. The treatment chamber 138 contains the object 206 to be treated with light as well as contaminated air from the non-sterile environment 142.

Also, while referring to FIG. 2F, the lamps 118 illuminate the object with light (Step 316 of FIG. 3). For example, in one embodiment, the Xenon flashlamps illuminate the object 206 with at least one, preferably two and most preferably three short duration pulses of high-intensity incoherent polychromatic light in a broad spectrum (e.g., 170 nm to 2600 nm). Preferably such light has at least 1% of its energy density concentrated at wavelengths within a range of 200 nm to 320 nm. As a result of such illumination, organisms on the surface of the object 206, contained within the air within the treatment chamber 138, and located underneath the periphery portion 150 of the flexible sheet 136 are effectively deactivated. Again, the transmissive barrier 120 is transmissive to the light emitted from the lamps 118. Reflector portions may be located behind the individual lamps 118 within the external shell to reflect additional light back into the treatment chamber 138. Note that in embodiments employing pulsed light lamps similar to those in U.S. patent application Ser. No. 09/580,361, the treatment chamber 138 may be accurately referred to as a sterilization chamber.

Furthermore, the inner surface of the sealed door 116 and the hatch body 132 may be reflective, i.e. second reflective inner surface 204 of the sealed door 116 and the first reflective inner surface 202 of the hatch body 132. Such reflective surfaces maximize the reflection of the light within the treatment chamber 138 to maximize the amount of sterilizing light that irradiates the object 206. Note that the flexible sheet 136 is positioned (and attached) over the first inner reflective surface 202, but is designed to be light transmissive; thus, the first reflective inner surface 202 still is able to reflect light since light will travel through the flexible sheet 136, be reflected off the first reflective inner surface 202 and travel back through the flexible sheet 136 into the treatment chamber 138.

Further advantageously, since the flexible sheet 136 is transmissive to the light provided by the lamps, any microorganisms that somehow get between the groove 112 and the periphery portion 150 of the flexible sheet 136 will also be deactivated during the light deactivation treatment. This is an important feature of this embodiment. Thus, this embodiment is able to sterilize the sealing surface between the opening of the treatment chamber 138 and the sealing surface of the "door", e.g. the hatch assembly 130. In contrast, the conventional sealed door systems of known passthrough devices are unable to treat surfaces between the opening of the treatment chamber 138 and the seal of the door. Disadvantageously, any microorganisms that manage to get in between the opening contact area and the door seal will not be deactivated by the light treatment and once the door is re-opened after light treatment, those microorganisms may escape back into a sterile environment, for example. This embodiment solves this problem by allowing the light treatment to penetrate the seal area between the door (i.e. the hatch assembly 130) and the contact area (i.e. the vacuum sterilizable sealing surface or the surface of the treatment chamber 138 that the hatch assembly 130 seals with). Thus, any trapped microorganisms are deactivated by the light treatment and can not be re-introduced into the sterile environment 141, for example.

Additionally, the inner surfaces of the first end wall 108 and the second end wall 110 may also be made to be reflective so as to further enhance the light reflecting within the treatment chamber 138. As such, in some embodiments, the inner surface of the groove 112 is reflective. Thus, the vacuum sterilizable sealing surface itself is reflective. In such embodiments, the sterilizing light will travel through the periphery portion 150 of the flexible sheet 136, reflect off of the inner surface of the groove 112 and travel back through the periphery portion 150 into the treatment chamber 138. This will further enhance the ability of the light treatment to deactivate any microorganisms trapped under the periphery portion 150 since the light reflecting from the reflective surface of the groove 112, for example, will also act on the microorganisms.

Next, referring to FIG. 2G, once the light treatment is finished, the treatment chamber 138 is unsealed from the sterile environment 141 (Step 318 of FIG. 3) by disengaging the vacuum pump, which unseals the periphery portion 150 of the flexible sheet 136 from the vacuum port 114 of the groove 112; thus, unsealing the vacuum-sealable hatch 130 from the first end wall 108. The vacuum-sealable hatch 130 is then removed from the treatment chamber 138 (Step 320 of FIG. 3) by pulling it out from the opening of the first end wall 108 into the sterile environment 141. Again, the flexible sheet 136 bends enough to easily remove the vacuum-sealable hatch 130 from the opening of the first end wall 108.

Note that in order to prevent air-borne microorganisms that were not deactivated during the pre-sterilization step from being re-introduced back into the treatment chamber 138, and thus, into the sterile environment 141, a pinch valve or switch is employed within the vacuum port 114. Such a pinch valve would allow air direction to flow in one direction only, thus, potentially contaminated air within the vacuum pump or vacuum port 114 would not enter the treatment chamber 138. Alternatively, a switch valve could be activated once the vacuum pump is to be disengaged to a clean air source (e.g., a sterile air source), such that any air drawing back into the treatment chamber 138 will be from the clean air source, not from within the vacuum pump 128.

Figure 2H:
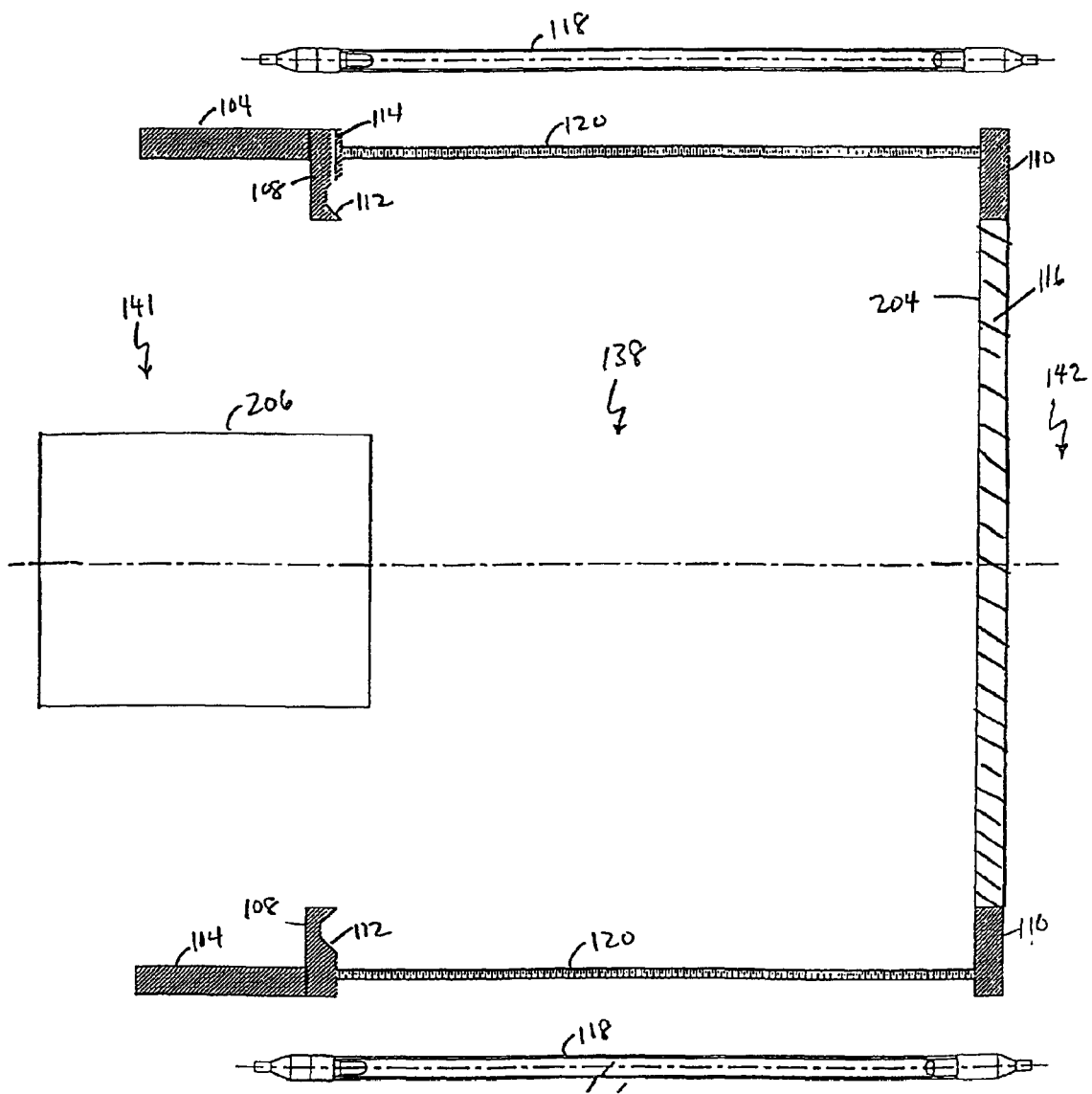

And finally, as shown in FIG. 2H, the object 206 to be sterilized is removed from the treatment chamber 138 into the sterile environment 141 (Step 322 of FIG. 3). Note that the sealed door 116 remains in position so that the non-sterile environment 142 remains sealed from the sterile environment 141 and the treatment chamber 138 remains sterilized. At this point, the system is ready to be reused starting back with FIG. 2B or Step 304 of FIG. 3, in which the vacuum-sealable hatch 130 is reinserted into the opening of the first end wall 108 in order to treat the next object to be passed into the sterile environment 141.

It is important to note that the steps accomplished in FIG. 3 may be slightly varied in the event the passthrough device is used as a rapid transport device that only has one opening for one vacuum-sealable hatch 130. Thus, the second end wall 110 does not include an opening and is permanently sealed against the end of the transmissive barrier 120. In such case, an object is placed into the treatment chamber 138 from an outside environment via the one opening (e.g. in the first end wall 108) which is then vacuum sealed similar to Steps 304 through 308 of FIG. 3, then treated according to Step 316 of FIG. 3, then removed into the outside environment similar to Steps 318 through 322 of FIG. 3.

Additionally, the vacuum-sealable hatch 130 may be used at the non-sterile environment 142 side of the passthrough device. For example, a non-sterile object is placed into the treatment chamber 138 from the non-sterile environment 142 with the treatment chamber 138 being sealed from the sterile environment 141. A vacuum-sealable hatch 130 is then positioned within the opening and caused to seal the treatment chamber 138 from the non-sterile environment 142 similar to Steps 304 through 308 of FIG. 3. Then, the object is treated with light similar to Step 316 of FIG. 3 (if pulsed light as described in U.S. patent application Ser. No. 09/580,361 is used, then the object is sterilized in Step 316), and then removed into the sterile environment by unsealing the sterile environment 141 from the treatment chamber 138 similar to Steps 318 through 322 of FIG. 3. This unsealing may involve disengaging another vacuum-sealable hatch 130 or opening a mechanically sealed door. Once this is done, the sterile environment 141 is then resealed from the treatment chamber 138 so that the vacuum-sealable hatch 130 may be unsealed from the non-sterile environment 142.

Figure 4:
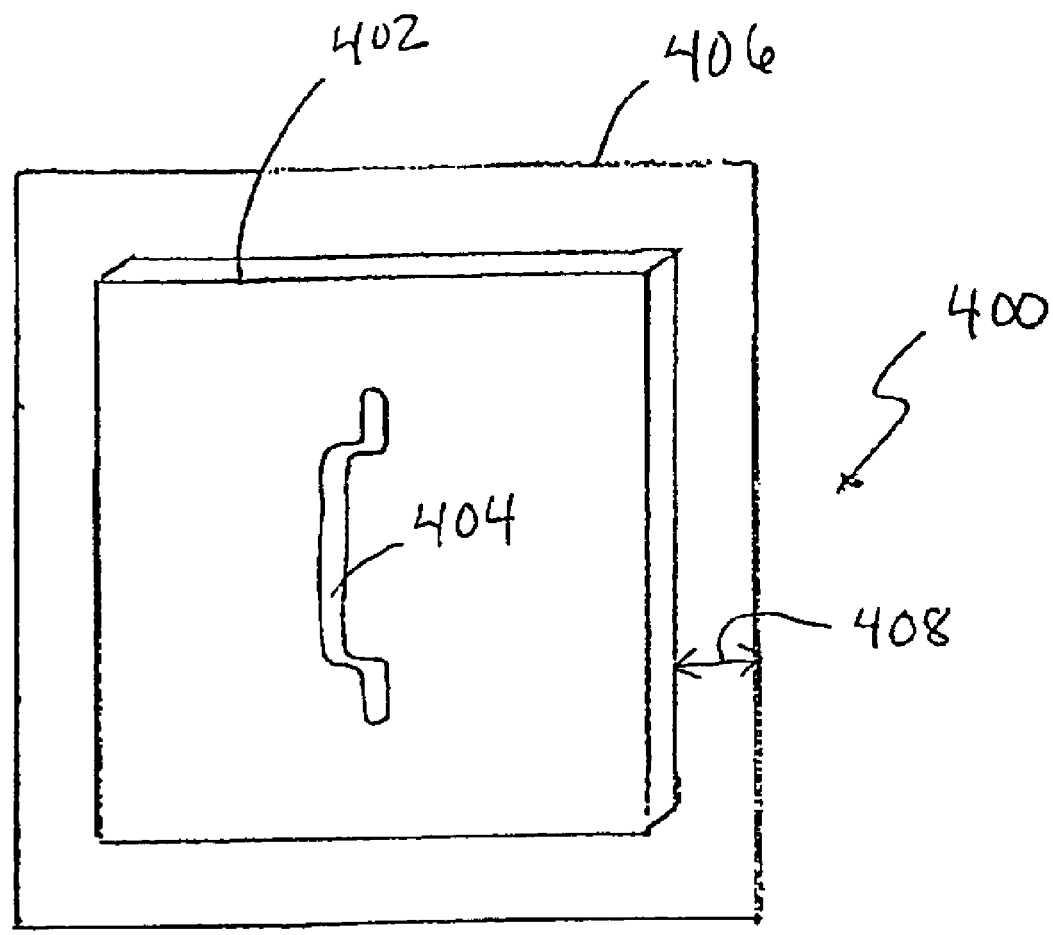
FIG. 4 is a view of another embodiment of the vacuum-sealable hatch of FIG. 1 having generally a square shape and used in another embodiment of the passthrough light treatment device of FIG. 1 having a square opening.

Referring next to FIG. 4, a view is shown of another embodiment of the vacuum-sealable hatch 130 of FIGS. 1 through 2H having generally a square cross section used in another embodiment of the passthrough device of FIGS. 1 through 2H. Shown is the vacuum-sealable hatch 400 including the hatch body 402, handle 404 and the flexible sheet 406 having periphery portion 408. In this embodiment of the present invention, the vacuum-sealable hatch 400 is square or rectangular in shape so that the vacuum-sealable hatch 400 may be inserted into a square or rectangular shaped opening of the end wall of the treatment chamber, e.g. a square shaped opening within the first end wall 108. It is noted that the volume within the treatment chamber could be a variety of geometric volumes, such as cuboid (or rectangular parallelepiped) or also could be cylindrical, as long as the opening in the end wall or other portion of the treatment chamber is generally square or rectangular in shape. Other geometric shapes could also be used for the vacuum-sealable hatch 400, such as a square, rectangle, octagon, etc.; however, the shape of the vacuum-sealable hatch 400 should generally conform to the shape of the opening to the treatment chamber, e.g. an opening of an end wall of the treatment chamber.

Figure 5A:
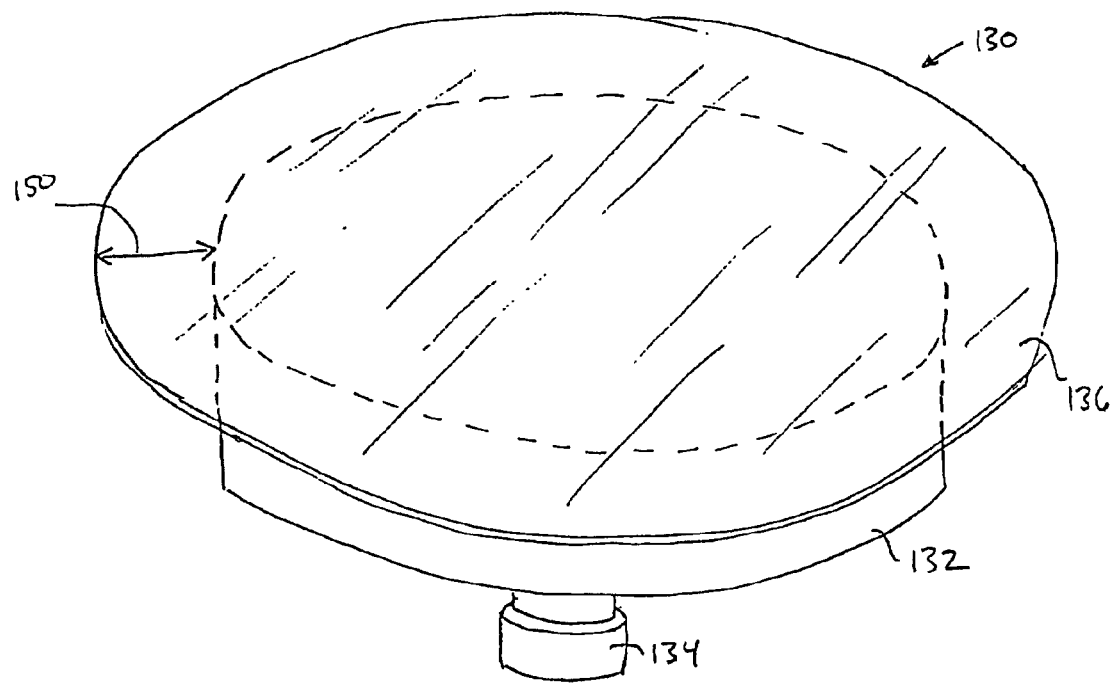
FIGS. 5A and 5B are perspective views of embodiments of the vacuum-sealable hatch of FIGS. 1 through 2H illustrating a flexible piece embodied as a flexible sheet and a flexible skirt, respectively.
Figure 5B:
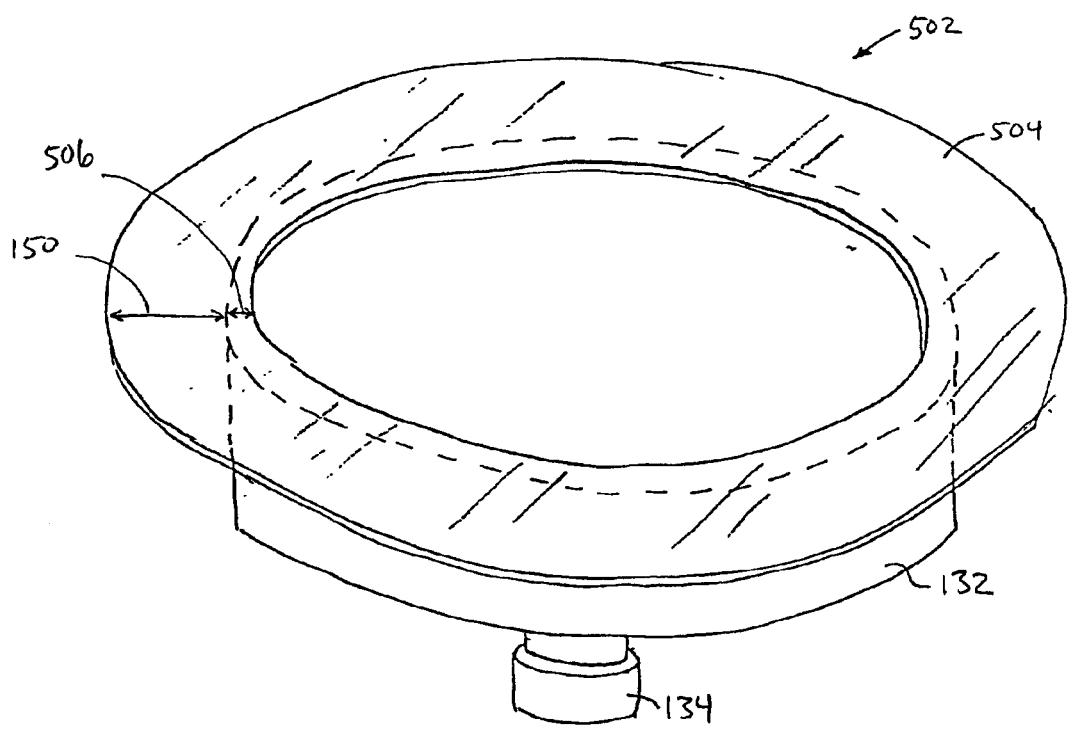

Referring next to FIGS. 5A and 5B, perspective views are shown of embodiments of the vacuum-sealable hatch of FIGS. 1 through 2H illustrating the flexible piece embodied as a flexible sheet and a flexible skirt, respectively. The embodiment of FIG. 5A illustrates the vacuum-sealable hatch 130 as described above including the hatch body 132, the handle 134 and the flexible piece, embodied as a flexible sheet 136. The flexible sheet 136 is light transmissive to the light used to treat objects within the treatment chamber. Additionally, the periphery portion 150 of the flexible sheet is illustrated as the portion of the flexible sheet 136 that extends beyond the outer dimension of the hatch body 132.

In the vacuum-sealable hatch 502 of FIG. 5B, the flexible piece takes the form of a flexible skirt 504 shaped as a ring with the central portion of the flexible sheet removed. The flexible skirt 504 embodiment includes the periphery portion 150 and also includes an attachment portion 506 that allows attachment of the flexible skirt 504 to the hatch body 132, e.g., using adhesives. In operation, this embodiment functions similarly to the vacuum-sealable hatch 130 of FIG. 5A. The vacuum-sealable hatch 502 of FIG. 5B should have slightly better reflectivity of light on the inner reflective surface of the hatch body, since the light does have to pass through a central portion of the flexible sheet, be reflected and then pass back through the central portion into the treatment chamber.

Figure 6:
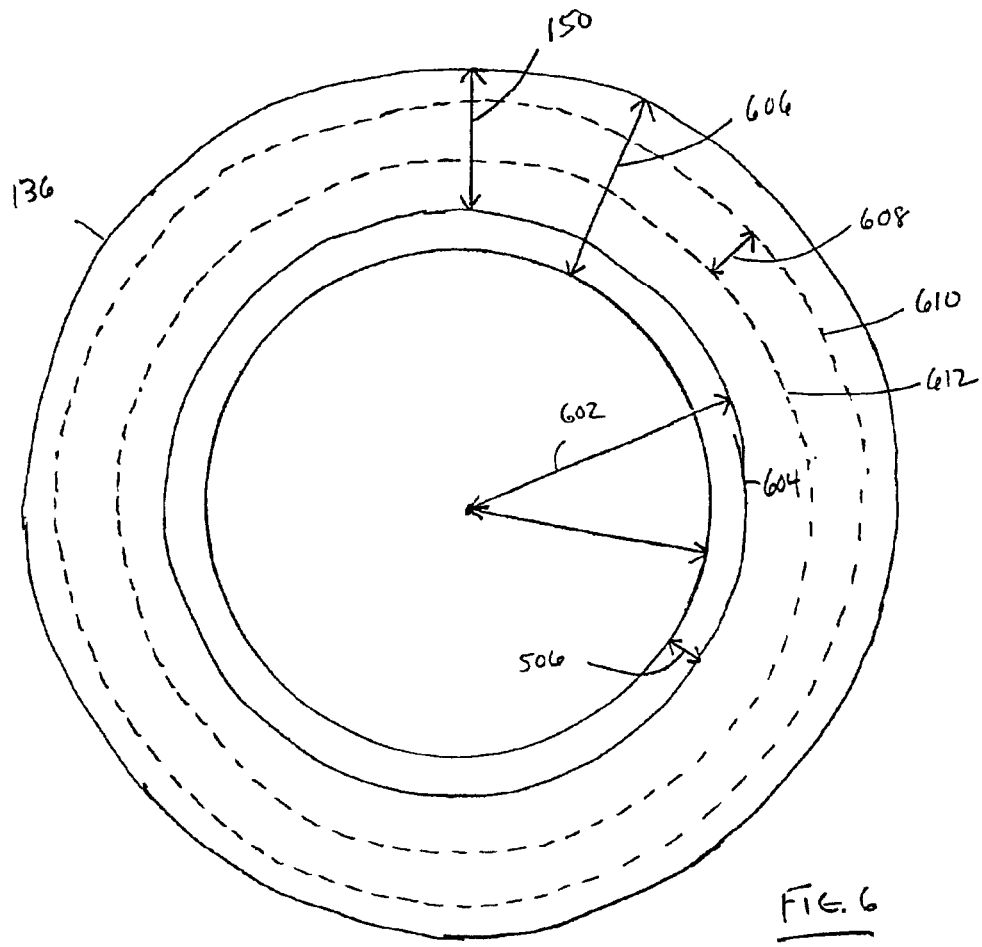
FIG. 6 is a diagram illustrating the various portions of a flexible sheet that may be used in one or more embodiments of the invention.

Referring next to FIG. 6, a diagram is shown illustrating the various portions of a flexible sheet that may be used in one or more embodiments of the invention. Illustrated is a circularly shaped flexible sheet 136 (referred to generically as a flexible piece) having a radius. The flexible sheet 136 includes several regions or portions. A central portion 602 is the portion of the flexible sheet that extends from the center of the flexible sheet 136 to the outer edge or outer dimension 602 of the hatch body (the profile of the hatch body is represented as outer dimension 604). A periphery portion 150 is the portion of the flexible sheet that extends beyond the outer dimension 602 of the hatch body 602, i.e., the portion of the flexible sheet 136 radially outside of the central portion 602. An attachment portion 506 is a portion of the central portion 602 from the outer dimension 602 of the hatch body and extending a determined amount radially toward the center. The attachment portion 506 is to provide a portion used to attach to the hatch body. A skirt portion 606 is a portion of the flexible sheet that includes the attachment portion 506 and the periphery portion 150. And finally, a seating region 608 is illustrated as a portion of the periphery portion 150 that is used to seat against (and seal to) a sealing surface of the treatment chamber. The seating region 608 is illustrated as between dashed concentric lines 610 and 612.

Figure 7:
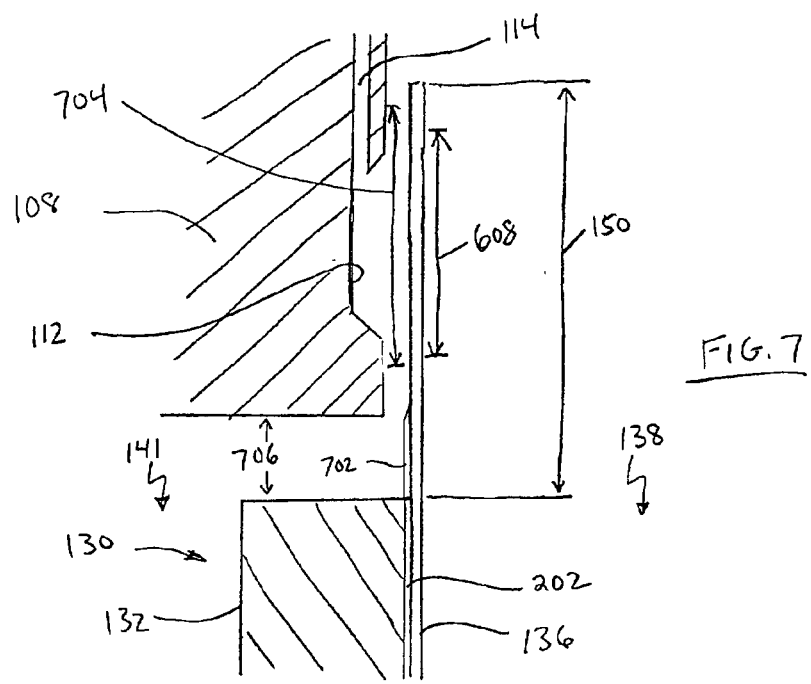
FIG. 7 is an enlarged cross sectional view of the seal area between an inner surface of the treatment chamber and one embodiment of the vacuum-sealable hatch.

Referring next to FIG. 7, an enlarged cross sectional view is illustrated of the seal area between an inner surface of the treatment chamber and one embodiment of the vacuum-sealable hatch. Illustrated is the first end wall 108, the groove 112, the vacuum port 114, the vacuum-sealable hatch 130 including the hatch body 132, the first reflective surface 202, and the flexible sheet 136. The flexible sheet 136 includes the periphery portion 150, the seating portion 608, and a coating 702. The first end wall 108 includes an inner surface that has a seating surface 704. Also shown is the spacing 706 between the outer dimension of the hatch body and the inner dimension of the opening in the first end wall 108.

Once the vacuum-sealable hatch is positioned within the opening of the treatment chamber (i.e., within the opening of the first end wall 108), the seating portion 608 of the flexible sheet 136 is positioned such that it will contact the seating region 704 of the inner surface of the treatment chamber (i.e, contact the seating region of an inner surface of the first end wall 108). Thus, when the vacuum pump is activated, the air is pulled from the groove 112 via the vacuum port 114 to tightly pull the seating portion 608 of the flexible sheet 136 against the seating region 704 of the first end wall 108. For example, the seating portion 608 is pulled into the groove 112.

Advantageously, in embodiments where the flexible sheet is light transmissive, the light treatment will deactivate microorganisms in between the flexible sheet 136 and the seating region 704 of the first end wall.

Furthermore, in order to prevent the light treatment from escaping out into the outside environment (e.g., the sterile environment) a coating 702 is applied to the outer side of the periphery portion that covers the spacing 706 formed between the outer dimension of the hatch body 132 and the opening of the first end wall 108. Advantageously, the coating 702 is not transmissive to the light treatment. The coating 702 may be a paint or other opaque coating. Thus, the light is prevented from escaping out of the treatment chamber 138 in to the sterile environment 141.

Figure 8D:
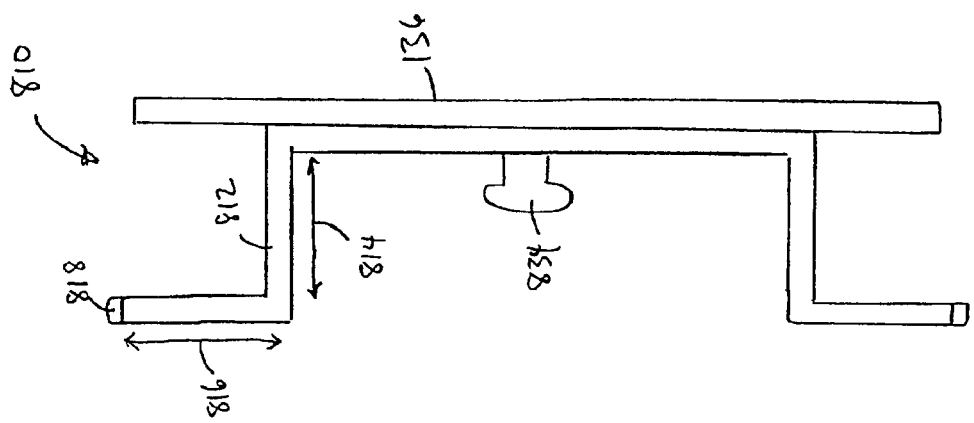
FIGS. 8A–8D are side views of several embodiments of the vacuum-sealable hatch.
Figure 8C:
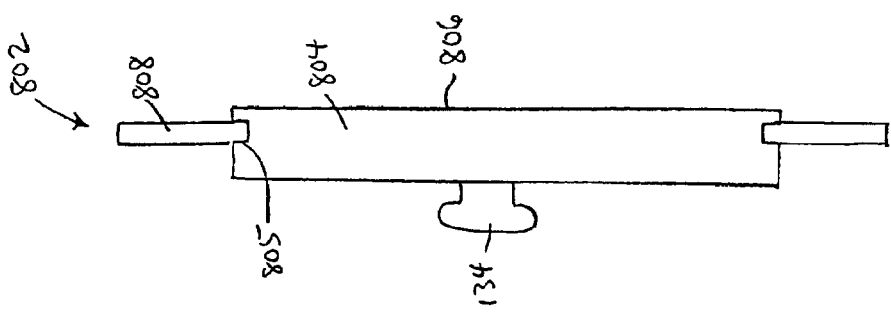
Figure 8B:
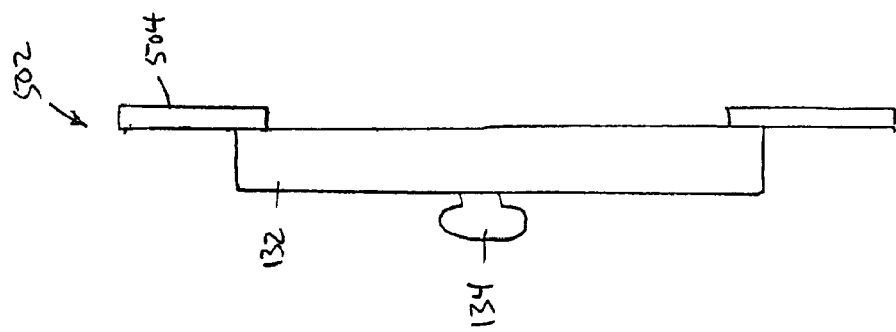
Figure 8A:
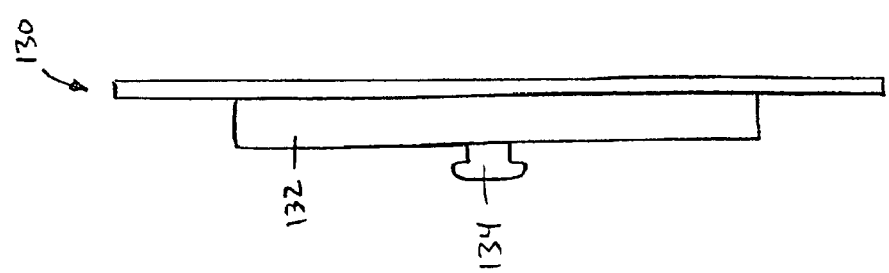

Referring next to FIGS. 8A–8D, side views of several embodiments of the vacuum-sealable hatch are illustrated. The vacuum-sealable hatch 130 of FIG. 8A is similar to those described above and includes the hatch body 132, the flexible sheet 136 and the handle 132. The vacuum-sealable hatch 502 of FIG. 8B illustrates the embodiment where the central portion of the flexible sheet is removed, leaving the skirt portion 504, i.e., the flexible skirt. It is noted that the thickness of the hatch body 132 may be varied to meet the specific design characteristics of the system. Furthermore, the flexible sheet 136 and the flexible skirt 502 are light transmissive in preferred embodiments. However, in alternative embodiments the flexible sheet 136 and the flexible skirt 504 may be opaque or not transmissive to the light treatment.

The vacuum-sealable hatch 802 of FIG. 8C illustrates an alternative embodiment where the hatch body 804 includes an annular ring 805 set into the thickness of the hatch body 804. The skirt portion 808 of this embodiment includes the periphery portion and the attachment portion; however, the attachment portion is pulled into the annular ring 805 extending about the hatch body 804. The attachment portion may be adhered within the annular ring 805 or simply held in place due to the elastic characteristics of the flexible skirt 808. This embodiment may also include a reflective surface 806 on the inner surface of the hatch body 804. This embodiment functions similarly to the embodiments as described above, even though it is attached to the hatch body 804 in a different manner.

The vacuum-sealable hatch 810 of FIG. 8D illustrates yet another embodiment where the hatch body 812 includes a neck portion 814 and a lip portion 816 that includes a seal 818 about the periphery of the lip portion 816. The neck portion 814 forms a hollow cylindrical tube that extends outerwardly from the treatment chamber. The flexible sheet 136 is attached to the inner end of the hatch body 812. The lip portion 816 is formed at the outer end of the neck portion 814 and appears as a washer shaped portion whose inside diameter is contiguous with the neck portion 814 and whose outside diameter extends radially away from the neck portion 814. At the periphery of the lip portion 816 is the seal 818. The seal 818 is an annular seal 818 extending circumferentially about the outer diameter of the lip portion 816. The function of the hatch body 812 of the embodiment of FIG. 8D is to prevent the light from entering the outside environment, e.g., the sterile environment if the vacuum-sealable hatch 810 is used on the sterile environment side of a treatment chamber. Further details are illustrated with reference to FIG. 9.

Figure 9:
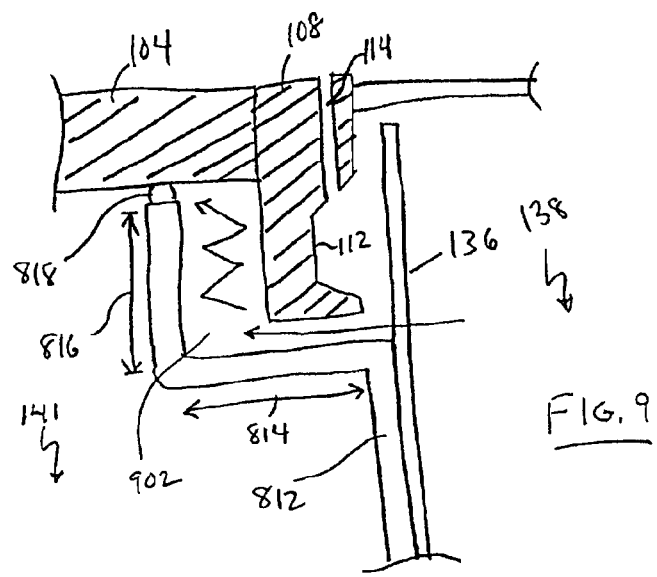
FIG. 9 is a cross sectional view of the vacuum-sealable hatch of FIG. 8D within the opening to the treatment chamber.

Referring next to FIG. 9, a cross sectional view is illustrated of the vacuum-sealable hatch of FIG. 8D within the opening to the treatment chamber. The lip portion 816 is sized such that when the hatch body 812 is inserted through the opening into the treatment chamber, the seal 818 contacts a surface of the isolator wall 104 (or other structure of the barrier isolator or enclosure to the sterile environment 141). The neck portion 814 is designed to have a length greater than the thickness of the opening in the first end wall 108 such that the flexible sheet 136 can be inserted fully into the treatment chamber 138 for sealing.

Advantageously, if any light escapes through the small spacing between the hatch body 108 and the first end wall 108, the light is contained within the volume 902. Volume 902 is the volume formed between the first end wall 108, the neck portion 814 and the lip portion 816 including the seal 818.

It is noted that some embodiments may also employ other means to contain the reflected light within the treatment chamber, such as using non-light transmissive materials for the flexible sheet, or for portions of the flexible sheet, or applying non-light transmissive coatings to the flexible sheet, as described above.

Figure 10:
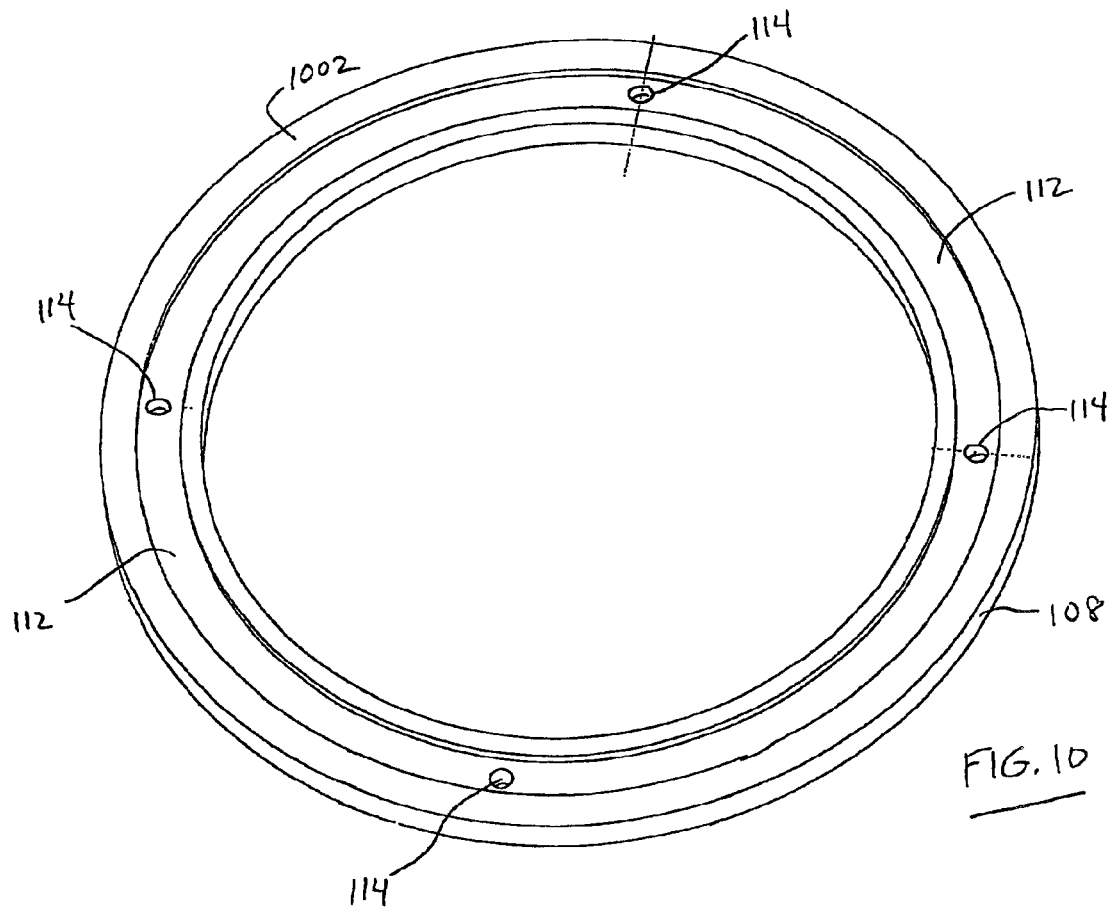
FIG. 10 is a perspective view of one embodiment of a vacuum sterilizable sealing surface of a light treatment chamber.

Referring next to FIG. 10, a perspective view is illustrated of one embodiment of a vacuum sterilizable sealing surface of a light treatment chamber. Shown is the interior surface 1002 of the first end wall 108 which includes the groove 112 and the vacuum ports 114. It is noted that the interior surface 1002 may be referred to generically as an "interior surface of a light treatment chamber". It is also noted that the surface of the groove 112 and the interior surface 1002 form a "seating region" which is adapted to seat and seal with a seating region of a flexible sheet or flexible skirt of the vacuum-sealable hatches of the several embodiments of the invention. The groove 112 is preferably trapezoidally shaped as described above and extends annularly about the interior surface 1002. The groove 112 also includes four vacuum ports 114 spaced about the groove 112. In alternative embodiments, it is noted that the groove 112 is not used and only the vacuum ports 114 are formed in the interior surface 1002 of the first end wall 108. Thus, in this embodiment, the seating region is interior surface 1002 including the vacuum ports 114. Additionally, the number of vacuum ports 114 formed is dependent upon the specific configuration of the system.

Figure 11:
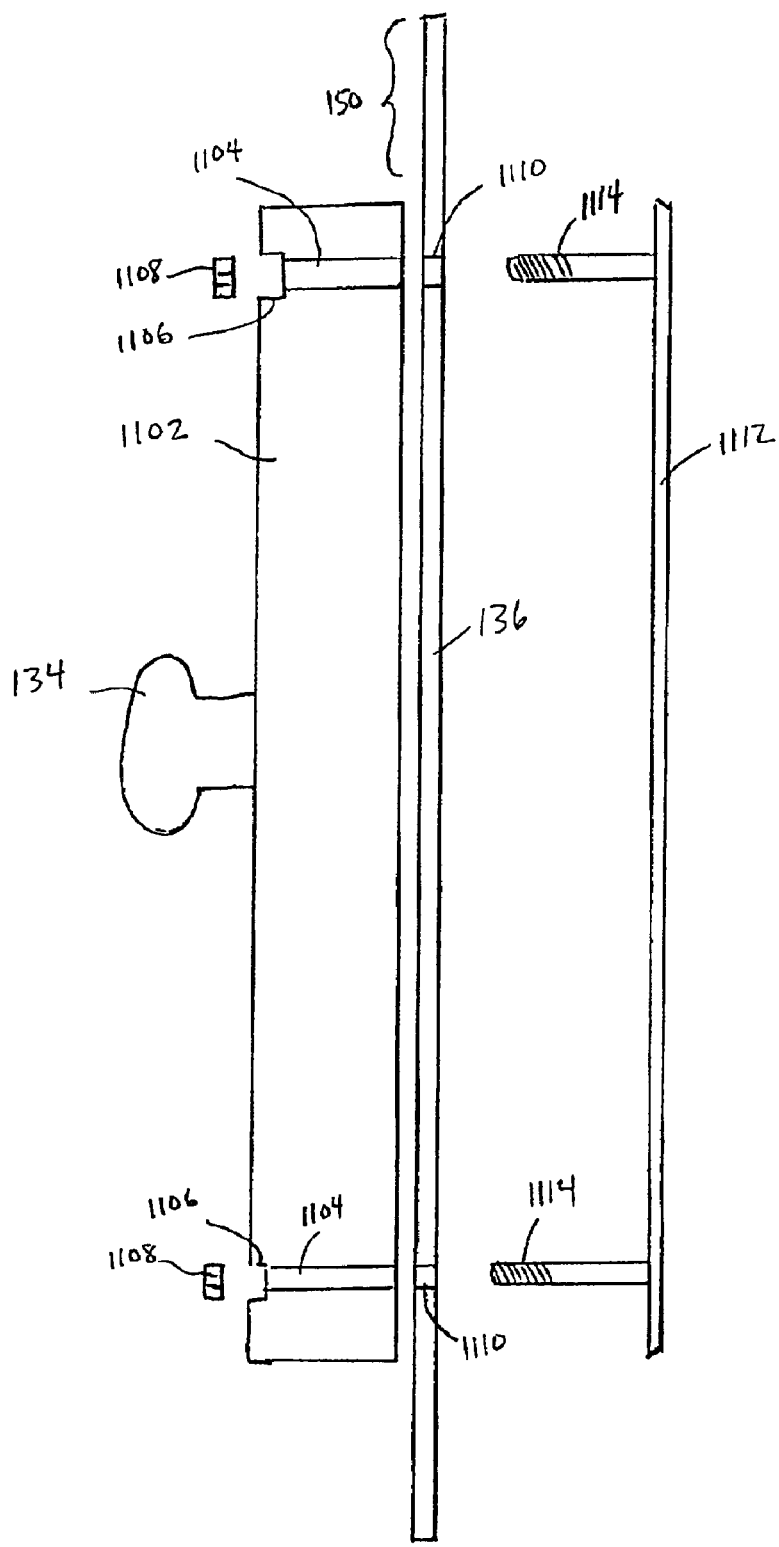
FIG. 11 is a side view of another embodiment of the vacuum sealable hatch of FIG. 1.

Referring next to FIG. 11, a side view of another embodiment of the vacuum sealable hatch of FIG. 1 is shown. In this embodiment, the hatch body 1102 includes shafts 1104 for receiving bolts 1114 (or screws) attached to a reflective piece 1112. The reflective piece 1112 has an exterior dimension generally conforming to the inner surface of the hatch body 1102 (i.e., the reflective piece 1112 has a circular shape matching the hatch body 1102). The reflective piece 1112 includes bolts 1114 that are attached to the side of the reflective piece that faces the hatch body 1102. Typically, the side of the reflective piece 1112 facing the hatch body 1102 is not reflective while the side of the reflective piece 1112 facing away from the hatch body 1102 is reflective in order to reflect light within the treatment chamber. The bolts are pressed through respective holes 1110 in the light transmissive flexible piece 136 and through the respective shafts 1104. Corresponding nuts 1108 are attached onto the bolts 1114 such that they sit within a respective recess 1106 formed within the hatch body 1102. It is understood that the bolts 1114 and nuts 1108 may be embodied many different ways. However, in this embodiment, the reflective piece 1112 is positioned over the flexible piece 136 such that the flexible piece 136 does not have to have a central portion removed and light within the treatment chamber is reflected directly off of the reflective piece 1112. Thus, the light does not have to pass through the flexible piece 136 and then reflect off of a surface underneath the flexible piece 136 back into the treatment chamber. The holes 1110 in the flexible piece 136 may be cut out, stamped out, punched out, or even formed by pressing the bolt 1114 through the flexible piece 136. Again, the flexible piece 136, and particularly the periphery portion 150 of the flexible piece are transmissive to the light within the treatment chamber such that surfaces underneath the periphery portion 150 are advantageously treated during the light treatment.

While the invention herein disclosed has been described by means of specific embodiments and applications thereof, numerous modifications and variations could be made thereto by those skilled in the art without departing from the scope of the invention set forth in the claims.

What is claimed is:

1. A vacuum-sealable hatch for sealing a treatment chamber from an outside environment comprising:
    a hatch body having at least a portion adapted to fit within an opening of the treatment chamber;

a flexible piece attached to the hatch body, wherein the flexible piece extends peripherally from the hatch body, wherein a seating portion of the flexible piece is adapted to be vacuum sealed to a seating region of an interior surface of the treatment chamber, wherein the hatch body and the flexible piece seal the treatment chamber from the outside environment, thereby preventing the free flow of microorganisms to and from the treatment chamber and the outside environment.

2. The vacuum-sealable hatch of claim 1 wherein the flexible piece comprises a flexible sheet.

3. The vacuum-sealable hatch of claim 2 wherein the flexible sheet comprises a central portion and a periphery portion, wherein the periphery portion includes the seating portion.

4. The vacuum-sealable hatch of claim 1 wherein the flexible piece comprises a flexible skirt.

5. The vacuum-sealable hatch of claim 4 wherein the flexible skirt comprises a periphery portion and an attachment portion, wherein the periphery portion includes the seating portion and the attachment portion is attached to the hatch body.

6. The vacuum-sealable hatch of claim 1 wherein the flexible piece is transmissive to light.

7. The vacuum-sealable hatch of claim 1 wherein at least the seating portion of the flexible piece is transmissive to light produced within the treatment chamber such that surfaces underneath the at least the seating portion are treated by the light.

8. The vacuum-sealable hatch of claim 1 wherein the flexible piece comprises a material selected from a group consisting of polyethylene, polypropylene, perfluoro ethylene propylene, perfluoro alkoxy alkane and ethylene vinyl acetate.

9. The vacuum-sealable hatch of claim 1 wherein an inner surface of the hatch body comprises a reflective inner surface.

10. The vacuum-sealable hatch of claim 1 further comprising an adhesive adhering the flexible piece to the hatch body.

11. The vacuum-sealable hatch of claim 1 further comprising a coating applied to a portion of the flexible piece, wherein the coating is not transmissive to light.

12. The vacuum-sealable hatch of claim 1 wherein the hatch body includes a neck portion extending from an end of the hatch body attached to the flexible piece, wherein the lip portion is formed at an outer end of the neck portion, wherein the lip portion includes a seal adapted to contact an outer surface of the treatment chamber to prevent light from escaping the treatment chamber.

13. The vacuum-sealable hatch of claim 1 wherein the hatch body includes an annular ring set into the hatch body, wherein the flexible piece attaches to the hatch body within the annular ring.

14. The vacuum-sealable hatch of claim 1 wherein the hatch body includes a reflective piece attached to the hatch body, wherein the flexible piece is positioned in between the reflective piece and the hatch body.

15. A hatch for sealing a light treatment chamber from an outside environment comprising:

a hatch body having at least a portion adapted to fit within an opening of the light treatment chamber;

a flexible piece attached to the hatch body, wherein the flexible piece extends peripherally from the hatch body, wherein a seating portion of the flexible piece is adapted to be sealed to a seating region of an interior surface of the light treatment chamber, wherein the hatch body and the flexible piece seal the light treatment chamber from the outside environment, wherein at least the seating portion of the flexible piece is light transmissive such that at least the seating region is treated by light from the light treatment chamber.

16. A light treatment device comprising:

a treatment chamber having an opening accessible from an outside environment and a seating region proximate to the opening;

one or more lamps within the treatment chamber for producing light within the treatment chamber, wherein the light is used to deactivate microorganisms within the treatment chamber;

one or more vacuum ports at the seating region;

a hatch body having at least a portion adapted to fit within the opening; and a flexible piece attached to the hatch body, the flexible piece having a periphery portion including a seating portion, wherein the periphery portion of the flexible piece overlaps the hatch body, wherein the seating portion is adapted to be vacuum sealed to the seating region;

wherein the hatch body and flexible piece seal the treatment chamber from the outside environment.

17. The device of claim 16 further comprising a vacuum pump coupled to the one or more vacuum ports.

18. The device of claim 16 further comprising another opening of the treatment chamber and a means for sealing the other opening from another outside environment.

19. The device of claim 18 wherein the outside environment comprises a substantially sterile environment and the other outside environment comprises a non-sterile environment.

20. The device of claim 16 further comprising a groove formed within the seating region, wherein the one or more vacuum ports are located within the groove.

21. The device of claim 20 wherein the groove has a trapezoidal cross section profile.

22. The device of claim 16 wherein the flexible piece is light transmissive to at least a portion of the light.

23. The device of claim 16 wherein at least the seating portion of the flexible piece is transmissive to light produced within the treatment chamber such that surfaces underneath the at least the seating portion are treated by the light.

24. The device of claim 16 wherein the flexible piece comprises a flexible sheet.

25. The device of claim 24 wherein the hatch comprises a reflective inner surface over which the light transmissive flexible sheet is attached.

26. The device of claim 16 wherein the flexible piece comprises a flexible skirt.

27. The device of claim 16 wherein an inner surface of the hatch body comprises a reflective inner surface.

28. The device of claim 16 further comprising an adhesive adhering the flexible piece to the hatch body.

29. The device of claim 16 wherein the seating region is located on an inner surface of an end wall of the treatment chamber.

30. The device of claim 16 wherein the seating region is reflective.

31. A sterilizable vacuum sealing surface of a treatment chamber of a light treatment device comprising:

an inner wall of the treatment chamber, wherein the treatment chamber defines a volume within which objects are treated with light for the reduction of microorganisms;

an opening formed within the inner wall, wherein the opening provides access to the treatment chamber from an outside environment;

a seating region of the inner wall, wherein the seating region is proximate to a periphery of the opening;

one or more vacuum ports at the seating region for forming a vacuum seal between the seating region and materials placed against the seating region.

32. The device of claim 31 wherein the seating portion of the inner wall is reflective.

33. The surface of claim 31 further comprising a groove formed within the seating region.

34. The device of claim 33 wherein the groove extends about an entire perimeter of the periphery of the opening.

35. A method of sealing a treatment chamber of a light treatment device from an outside environment comprising:

placing at least a portion of a hatch body within an opening of the treatment chamber, wherein the hatch body includes a flexible piece attached to the hatch body, wherein a periphery portion of the flexible piece overlaps the hatch body;

positioning the at least the portion of the hatch body within the opening such that a seating portion of the periphery portion is within the treatment chamber and contacts an inner surface of the treatment chamber; and creating a vacuum seal between the inner surface of the treatment chamber and the seating portion of the flexible piece, wherein the flexible piece and the hatch body seal the treatment chamber from the outside environment.

36. The method of claim 35 further comprising treating the inner surface of the treatment chamber that is covered by the periphery portion with light from within the treatment chamber.

37. The method of claim 35 wherein the creating further comprises creating the vacuum seal between one or more vacuum ports located on the inner surface of the treatment chamber and the seating portion of the flexible piece, wherein the one or more vacuum ports are proximate to a periphery of the opening.

38. The method of claim 37 wherein the creating further comprises creating the vacuum seal between the one or more vacuum ports located within a groove formed within the inner surface and the seating portion of the flexible piece, wherein the groove is located proximate to the periphery of the opening.

39. A method of treating and passing an object from a non-sterile environment into a substantially sterile environment comprising:

pre-sterilizing a treatment chamber;

vacuum sealing the treatment chamber from the substantially sterile environment;

placing the object into the treatment chamber from the non-sterile environment;

sealing the non-sterile environment from the treatment chamber;

illuminating the object with light, wherein organisms present on the object are deactivated;

unsealing the treatment chamber from the substantially sterile environment; and removing the object from the treatment chamber into the substantially sterile environment.

40. The method of claim 39 wherein said illuminating comprises illuminating surfaces covered by a vacuum seal used in the vacuum sealing step.

41. The method of claim 39 further comprising sealing, prior to said pre-sterilizing, the treatment chamber from the non-sterile environment.

42. The method of claim 41 further comprising unsealing, prior to said placing and after said vacuum sealing, the treatment chamber from the non-sterile environment.

43. The method of claim 39 wherein said vacuum sealing comprises creating a vacuum seal between a flexible piece and an inner surface of the treatment chamber, wherein the flexible piece is attached to a hatch body and comprises a periphery portion that overlaps the hatch body.

44. The method of claim 39 further comprising:

placing, prior to said vacuum sealing, a hatch body within an opening of the treatment chamber, wherein the hatch body includes a flexible piece attached to the hatch body, wherein a periphery portion of the flexible piece overlaps the hatch body; and positioning the hatch body within the opening such that a seating portion of the periphery portion is within the treatment chamber and contacts an inner surface of the treatment chamber.

45. The method of claim 44 wherein said vacuum sealing comprises creating a vacuum seal between the inner surface of the treatment chamber and the seating portion of the periphery portion, whereby vacuum sealing the treatment chamber from the substantially sterile environment.

46. The method of claim 45 wherein said creating further comprises creating the vacuum seal between one or more vacuum ports located on the inner surface of the treatment chamber and the portion of the flexible piece, wherein the one or more vacuum ports are located proximate to a periphery of the opening.

47. The method of claim 45 wherein the creating further comprises creating the vacuum seal between one or more vacuum ports located within a groove formed within the inner surface of the treatment chamber and the seating portion, wherein the groove is located proximate to a periphery of the opening.

48. The method of claim 45 further comprising activating, prior to the creating, a vacuum pump coupled to the one or more vacuum ports.

* * * * *